United States Patent
Weir

(10) Patent No.: US 10,987,384 B2
(45) Date of Patent: Apr. 27, 2021

(54) REACTION PLATFORM AND METHOD FOR MAKING POLLEN BASED MATERIALS AND USES THEREOF

(71) Applicant: DECIMA HEALTH LIMITED, Christchurch (NZ)

(72) Inventor: Iona Weir, Auckland (NZ)

(73) Assignee: DECIMA HEALTH LIMITED, Christchurch (NZ)

(*) Notice: Subject to any disclaimer, the term of this patent is extended or adjusted under 35 U.S.C. 154(b) by 0 days.

(21) Appl. No.: 16/578,661

(22) Filed: Sep. 23, 2019

(65) Prior Publication Data

US 2020/0061126 A1 Feb. 27, 2020

Related U.S. Application Data

(60) Division of application No. 15/884,058, filed on Jan. 30, 2018, now Pat. No. 10,434,123, which is a continuation-in-part of application No. 14/911,652, filed as application No. PCT/IB2014/002786 on Aug. 12, 2014, now Pat. No. 9,877,991.

(60) Provisional application No. 61/865,011, filed on Aug. 12, 2013.

(51) Int. Cl.
| | | |
|---|---|---|
| *A61K 36/00* | (2006.01) | |
| *A61K 35/644* | (2015.01) | |
| *A61K 8/98* | (2006.01) | |
| *A61K 8/92* | (2006.01) | |
| *A61Q 19/00* | (2006.01) | |
| *A61P 17/06* | (2006.01) | |
| *A61P 29/00* | (2006.01) | |
| *A61K 9/00* | (2006.01) | |
| *A61K 9/06* | (2006.01) | |
| *A61K 31/07* | (2006.01) | |
| *A61K 31/355* | (2006.01) | |
| *A61K 31/375* | (2006.01) | |
| *A61K 31/60* | (2006.01) | |
| *A61K 47/10* | (2017.01) | |
| *A61K 47/14* | (2017.01) | |
| *A61K 47/20* | (2006.01) | |
| *A61K 47/44* | (2017.01) | |

(52) U.S. Cl.
CPC ............ *A61K 35/644* (2013.01); *A61K 8/927* (2013.01); *A61K 8/988* (2013.01); *A61K 9/0014* (2013.01); *A61K 9/06* (2013.01); *A61K 31/07* (2013.01); *A61K 31/355* (2013.01); *A61K 31/375* (2013.01); *A61K 31/60* (2013.01); *A61K 36/00* (2013.01); *A61K 47/10* (2013.01); *A61K 47/14* (2013.01); *A61K 47/20* (2013.01); *A61K 47/44* (2013.01); *A61P 17/06* (2018.01); *A61P 29/00* (2018.01); *A61Q 19/00* (2013.01); *A61K 2236/19* (2013.01); *A61K 2236/51* (2013.01); *A61K 2800/84* (2013.01); *A61K 2800/85* (2013.01)

(58) Field of Classification Search
None
See application file for complete search history.

(56) References Cited

U.S. PATENT DOCUMENTS

| | | | |
|---|---|---|---|
| 4,746,071 A | 5/1988 | Grunhoff et al. | |
| 6,270,811 B1 | 8/2001 | Fregonese | |
| 6,482,442 B1 | 11/2002 | Dado | |
| 7,288,265 B1 | 10/2007 | Rolf | |
| 10,434,123 B2 | 10/2019 | Weir | |
| 2004/0258765 A1 | 12/2004 | Gee | |
| 2006/0172022 A1 | 8/2006 | Szanzer | |
| 2007/0098671 A1 | 5/2007 | Martin | |
| 2007/0141168 A1 | 6/2007 | Alkazemi | |
| 2009/0291122 A1 | 11/2009 | Vandeputte | |
| 2010/0272790 A1 | 10/2010 | Morariu | |
| 2012/0156673 A1 | 6/2012 | De Lucca et al. | |
| 2013/0011349 A1 | 1/2013 | Tawashi et al. | |
| 2016/0193263 A1 | 7/2016 | Weir | |
| 2018/0185419 A1 | 7/2018 | Weir | |

FOREIGN PATENT DOCUMENTS

| | | | |
|---|---|---|---|
| CN | 1072955 A | | 6/1993 |
| CN | 1165637 A | | 11/1997 |
| CN | 101491649 A | * | 7/2009 |
| CN | 103053893 A | | 7/2012 |
| CN | 102784171 A | | 11/2012 |

(Continued)

OTHER PUBLICATIONS

U.S. Patent and Trademark Office International Search Authority, "International Search Report" and "Written Opinion" dated Jul. 17, 2019 in PCT Application No. PCT/IB19/50726.
Gaze, P.D., et al., Honeydew and Its Importance to Birds in Beech Forests of South Island, New Zealand. New Zealand Journal of Ecology. 1983; 6: 33-37.

(Continued)

*Primary Examiner* — Qiuwen Mi
(74) *Attorney, Agent, or Firm* — Barnes & Thornburg LLP

(57) ABSTRACT

A fermented pollen-based composition is provided which is made by treating pollen grains with one or more natural potassium sources selected from coconut water, coconut milk, raw honey, or honeydew honey, to naturally stimulate germination of the pollen, then incubating the germinated pollen, optionally with one or more additional components selected from beeswax, oils, enzyme-containing components derived from fruit, and probiotic components, wherein the resulting composition comprises a plurality of bioactive components selected from low molecular weight peptides, fatty acids, esterified flavonoids, dicaffeoyl quinic acid isomers and dicaffeoyl tartaric acid ester or ether compounds. Topical skin compositions including the fermented pollen-based composition as an active ingredient are also provided.

14 Claims, 14 Drawing Sheets

(56) References Cited

FOREIGN PATENT DOCUMENTS

| EP | 0136479 | A2 | 4/1985 |
|---|---|---|---|
| EP | 0319062 | B1 | 2/1992 |
| EP | 654262 | A1 | 5/1995 |
| EP | 2824168 | B1 | 9/2015 |
| GB | 2485483 | A | 5/2012 |
| WO | 1999059523 | A2 | 11/1999 |
| WO | 2002032442 | A1 | 4/2002 |
| WO | 2012092673 | A1 | 7/2012 |

OTHER PUBLICATIONS

O'Brien, IE, et al., Annexin-V and TUNEL Use in Monitoring the Progression of Apoptosis in Plants. Cytometry. Sep. 1, 1997; 29:28-33.

O'Brien, IE, et al., Early Stages of the Apoptotic Pathway in Plant Cells are Reversible. The Plant Journal. 1998; 13(6), 803-814.

O'Brien, IE, et al., Protoplasts to Plants of Gentianaceae. Regeneration of Lisianthus (*Eustoma grandiflorum*) is Affected by Calcium Ion Preconditioning, Osmolality and pH of Culture Media. Apr. 1993; 33(1): 31-37. Abstract Only.

Weir, et al. Oxidative Stress is Generated via the Mitochondrial Respiratory Chain During Plant Cell Apoptosis. Cytometry. Aug. 2003; Part A 54A:109-117.

Loden, M., et al., "A double-blind study comparing the effect of glycerine and uerea on dry,eczematous skin in atopic patients." Acta Derm Venereol 2002; 82: 45-47.

Krafchik B.R. et al., "Eczema" Paediatr Child Health 2005; 5(2): 101-105.

Sohn, BA Andrew et al., "Eczema" Mt Sinai J Med 78:730-739, 2011. Abstract Only.

Eberlein, B. et al., "Adjuvant treatment of atopic eczema: assessment of an emollient containing N-palmitoylethanolamine (ATOPA study)" Eur Acad Dermatol Venereol. Jan. 2008;22(1):73-82. Abstract Only.

* cited by examiner

| | | |
|---|---|---|
| Customer Sample ID | | V-TP Fermented Pollen |
| NZLABS Sample Number | | 2387629 |
| Date Sampled | | 08/04/2011 |
| Test/Reference | Unit | |
| Fatty acid profile AOAC991.39/969.33/963.22 | | |
| C4:0 (Butyric acid) | g/100g | <0.5 |
| C5:0 (Valeric acid) | g/100g | <0.5 |
| C6:0 (Caproic acid) | g/100g | <0.5 |
| C7:0 (Enanthic acid) | g/100g | <0.5 |
| C8:0 (Caprylic acid) | g/100g | <0.5 |
| C9:0 (Pelargonic acid) | g/100g | <0.5 |
| C10:0 (Capric acid) | g/100g | <0.5 |
| C11:0 (Undecylic acid) | g/100g | <0.5 |
| C12:0 (Lauric acid) | g/100g | 0.8 |
| C13:0 (Tridecylic acid) | g/100g | <0.5 |
| C14:0 (Myristic acid) | g/100g | 0.5 |
| C14:1cis (Myristoleic acid) | g/100g | <0.5 |
| C15:0 (Pentadecylic acid) | g/100g | <0.5 |
| C15:1cis | g/100g | <0.5 |
| C16:0 (Palmitic acid) | g/100g | 25.2 |
| C16:1trans (Palmitelaidic acid) | g/100g | <0.5 |
| C16:1cis (Palmitoleic acid) | g/100g | 0.6 |
| C17:0 (Margaric acid) | g/100g | <0.5 |
| C17:1cis | g/100g | <0.5 |
| C18:0 (Stearic acid) | g/100g | 1.6 |
| C18:1trans (Elaidic acid) | g/100g | <0.5 |
| C18:1cis (Oleic acid) | g/100g | 7.1 |
| C18:2trans (Linelaidic acid) | g/100g | 0.0 |
| C19:0 (Nondecylic acid) | g/100g | <0.5 |
| C18:2 cis (Linoleic acid) | g/100g | 23.0 |
| C20:0 (Arachidic acid) | g/100g | <0.5 |
| C18:3 (GLA) | g/100g | 0.8 |
| C18:3 cis (Linolenic acid) | g/100g | 34.2 |
| C20:1 cis (Eicosenoic acid) | g/100g | <0.5 |
| C21:0 (Heneicosanoic acid) | g/100g | <0.5 |
| C22:0 (Behenic acid) | g/100g | 0.7 |
| C20:2 cis | g/100g | <0.5 |
| C20:3 cis | g/100g | <0.5 |
| C22:1 cis | g/100g | <0.5 |

FIG. 1

| Test/Reference | Unit | |
|---|---|---|
| C20:4 | g/100g | <0.5 |
| C23:0 (Tricosanoic acid) | g/100g | <0.5 |
| C22:2 cis | g/100g | <0.5 |
| C20:5 (EPA) | g/100g | <0.5 |
| C24:0 (Lignoceric acid) | g/100g | 1.2 |
| C24:1 cis | g/100g | <0.5 |
| C22:5 cis (DPA) | g/100g | <0.5 |
| C22:6 cis (DHA) | g/100g | <0.5 |
| Unidentified fatty acids | g/100g | 0.9 |

Test Comments

| 2387629 | Fatty acid profile | C11:1C (Methyl Undecenoate) 0.125g/100g, C12:1C (Methyl Dodecenoate) 0.752g/100g & C18:1n7c ((Methyl Vaccenate) 1.133g/100g also present in the sample. |

FIG. 1 Cont'd.

| Customer Sample ID | | Fermented Pollen upper layer | Fermented Pollen sediment |
|---|---|---|---|
| NZLABS Sample Number | | 2366630 | 2376545 |
| Date Sampled | | 24/03/2011 | 24/03/2011 |
| Test/Reference | Unit | | |
| Fatty acid profile AOAC991.39/969.33/963.22 | | | |
| C4:0 (Butyric acid) | g/100g | <0.5 | <0.5 |
| C5:0 (Valeric acid) | g/100g | <0.5 | <0.5 |
| C6:0 (Caproic acid) | g/100g | <0.5 | <0.5 |
| C7:0 (Enanthic acid) | g/100g | <0.5 | <0.5 |
| C8:0 (Caprylic acid) | g/100g | <0.5 | <0.5 |
| C9:0 (Pelargonic acid) | g/100g | <0.5 | <0.5 |
| C10:0 (Capric acid) | g/100g | <0.5 | <0.5 |
| C11:0 (Undecylic acid) | g/100g | <0.5 | <0.5 |
| C12:0 (Lauric acid) | g/100g | 3.1 | 2.5 |
| C13:0 (Tridecylic acid) | g/100g | <0.5 | <0.5 |
| C14:0 (Myristic acid) | g/100g | 1.1 | <0.5 |
| C14:1 cis (Myristoleic acid) | g/100g | <0.5 | <0.5 |
| C15:0 (Pentadecylic acid) | g/100g | <0.5 | <0.5 |
| C15:1 cis | g/100g | <0.5 | <0.5 |
| C16:0 (Palmitic acid) | g/100g | 24.2 | 27.6 |
| C16:1 trans (Palmitelaidic acid) | g/100g | <0.5 | <0.5 |
| C16:1 cis (Palmitoleic acid) | g/100g | <0.5 | <0.5 |
| C17:0 (Margaric acid) | g/100g | <0.5 | <0.5 |
| C17:1 cis | g/100g | <0.5 | <0.5 |
| C18:0 (Stearic acid) | g/100g | 4.0 | 1.6 |
| C18:1 trans (Elaidic acid) | g/100g | <0.5 | <0.5 |
| C18:1 cis (Oleic acid) | g/100g | 5.4 | 3.5 |
| C18:2 trans (Linoelaidic acid) | g/100g | 0.0 | 0.0 |
| C19:0 (Nonadecylic acid) | g/100g | <0.5 | <0.5 |
| C18:2 cis (Linoleic acid) | g/100g | 17.5 | 21.6 |
| C20:0 (Arachidic acid) | g/100g | <0.5 | <0.5 |
| C18:3 (GLA) | g/100g | <0.5 | 1.3 |
| C18:3 cis (Linolenic acid) | g/100g | 24.5 | 35.0 |
| C20:1 cis (Eicosenoic acid) | g/100g | <0.5 | <0.5 |
| C21:0 (Heneicosanoic acid) | g/100g | <0.5 | <0.5 |
| C22:0 (Behenic acid) | g/100g | <0.5 | <0.5 |
| C20:2 cis | g/100g | <0.5 | <0.5 |
| C20:3 cis | g/100g | <0.5 | <0.5 |
| C22:1 cis | g/100g | <0.5 | <0.5 |

FIG. 2

| Test/Reference | Unit | |
|---|---|---|
| C20:4 | g/100g | <0.5 |
| C23:0 (Tricosanoic acid) | g/100g | <0.5 |
| C22:2 cis | g/100g | <0.5 |
| C20:5 (EPA) | g/100g | <0.5 |
| C24:0 (Lignoceric acid) | g/100g | 1.2 |
| C24:1 cis | g/100g | <0.5 |
| C22:5 cis (DPA) | g/100g | <0.5 |
| C22:6 cis (DHA) | g/100g | <0.5 |
| Unidentified fatty acids | g/100g | 0.9 |

Test Comments

| 2387629 | Fatty acid profile | C11:1C (Methyl Undecenoate) 0.125g/100g ,C12:1C (Methyl Dodecenoate) 0.752g/100g &C18:1n7c ((Methyl Vaccenate) 1.133g/100g also present in the sample. |
|---|---|---|

REACTION PLATFORM AND METHOD FOR MAKING POLLEN BASED MATERIALS AND USES THEREOF

This application is a divisional of U.S. application Ser. No. 15/884,058, filed on Jan. 30, 2018, which is a continuation-in-part of U.S. application Ser. No. 14/911,652, filed on Feb. 11, 2016, now U.S. Pat. No. 9,877,991, which is a U.S. National Stage application under 35 U.S.C. § 371 of International Application No. PCT/IB2014/002786, filed on Aug. 12, 2014, which claims the benefit of earlier filed U.S. Provisional Application No. 61/865,011, filed on Aug. 12, 2013, each of which are hereby incorporated by reference herein.

FIELD OF THE INVENTION

A process for making pollen-based products is described in connection with a reaction platform. Cosmetic and nutraceutical formulations containing pollen-based materials, including polypeptides, amino acids, fatty acid triglycerides and flavanoids in combination with beeswax suitable for administration to an individual are described.

BACKGROUND

Beehives in the natural state comprise interesting chemistry including release of valuable bioactive components of pollen that is transported into the hive, by the action of certain enzymes. However, use of the raw materials or mixtures of the beehive presents problems including separation of components, contamination by microbial flora, and/or exposure to pesticides used to eradicate pests such as mites. Thus, a method is needed to economize yet streamline production using the desired beehive components in synergistic combinations.

The present inventor (Weir, formerly known as O'Brien) has shown that plants possess internal genetic mechanisms to control the process and progression of apoptosis, also known as programmed cell death (PCD). In one instance, chromatin condensation, which is a hallmark of PCD in mammalian cells, may be reversible in plant cells during the early stages of apoptosis (O'Brien, et al., *The Plant Journal* (1998) 13(6): 803-814).

Pollen has a hard shell known as the sporopollenin which is very resistant to chemical degradation. Also on the surface of the pollen are proteins which cause known allergies. In one method a reaction is used to "explode" or "crack" the pollen grains under pressure followed by a protease to hydrolyse and deactivate the allergy producing proteins.

In another possible two-step reaction, pollen may be manipulated to begin germination and thus release the bioactive contents of the pollen more gently and naturally.

Therefore, if a way could be found to first open or germinate pollen grains to release beneficial components in a biotic manner, followed by addition of other beehive components, this would mimick a natural process, yet provide a novel way to obtain nutraceutical or cosmetic products.

Atopic dermatitis, commonly known as eczema, is a complex skin disease that is characterized by pruritus, disrupted epidermal barrier function, and immunoglobulin sensitization to various food and environmental allergens (Sohn, A., et al., "Eczema," *Mt. Sinai J. Med.* (2011) 78:730-739). Inflammation of the skin appears like erythema, which may include scaling and crusts (Krafchik, B. R., "*Eczema,*" *Paediatr. Child Health* (2000) 5:101-105). It usually occurs due to the interaction of the genes with the environment. Patients with eczema develop a higher risk for skin infections. Skin care products including moisturizing creams are being used to treat dry and scaly skin (Loden, M., et al., "A double-blind study comparing the effect of glycerine and urea on dry, eczematous skin in atopic patients," *Acta Derm. Venereol.* (2002) 82:45-47). Effectiveness of such creams indicated a positive effect on the quality of life of the patients who tried the products (Eberlein, B., et al., "Adjuvant treatment of atopic eczema: assessment of an emollient containing N-palmitoylethanolamine (ATOPA study)," *J. Eur. Acad. Dermatol. Venereol.* (2008) 22:73-82).

If a way could be found to use plant-based materials to affect or control immune or PCD signaling pathways in mammalian cells, this would constitute a valuable contribution to the nutraceutical and medical arts.

Further, if a way could be found to use plant-based materials including pollen-based extracts for treating inflammatory or skin conditions, this would constitute a valuable contribution to the nutraceutical, cosmetic, and medical arts.

SUMMARY OF THE INVENTION

A pollen-based extract includes germinated pollen, beehive components, and optionally enzyme-containing material including honeydew or plant powders.

An aqueous skin cream includes the pollen-based extract and one or more of glycerine, natural oils, emollients, preservatives, vitamins, fragrance, emulsifiers, or waxes. The skin cream may be used for treatment of skin conditions or inflammation.

A method of treating eczema or psoriasis is provided, comprising administering to the individual in need of such treatment a therapeutically effective amount of an aqueous skin cream. The skin cream may be applied topically to the skin.

A two stage reaction platform is provided to produce a pollen-based extract material, comprising the steps of a first stage including: opening and/or germinating pollen grains, reacting the treated pollen grains with one or more beehive components, selected from beeswax, honey, or enzyme-containing material, and stirring to form a jelly; and a second stage including heating the jelly in a closed container to product an extract. The extract may be a fermented extract. It is understood that the extract may be further fermentable by the addition of one or more components.

In a particular embodiment, pollen is incubated in coconut water to produce a fermented pollen-based extract.

In one embodiment, a process for making a pollen-based fermentable composition includes (a) soaking dry pollen grains in coconut water at ambient temperature to provide soaked pollen; (b) treating the soaked pollen at ambient temperature to provide a germinated pollen mixture; and (c) incubating the germinated pollen mixture in a sealed vessel for about 6 hours to about 24 hours at 37° C. to produce the fermented pollen-based composition. Optionally, propolis is used to halt the fermentation.

In another embodiment, an oil or a beeswax is added in a layer on top of the germinated pollen mixture to create an anaerobic medium, after which the incubating step is carried out to effect fermentation. Optionally, propolis is used to halt the fermentation.

BRIEF DESCRIPTION OF THE DRAWINGS

FIG. 1 depicts a fatty acid analysis of the opened and fermented pollen prepared according to an embodiment of the present invention.

FIG. 2 depicts a fatty acid analysis of the opened and fermented pollen (both upper layer from reaction and sediment) prepared according to an embodiment of the present invention.

DETAILED DESCRIPTION

Figure 3A:
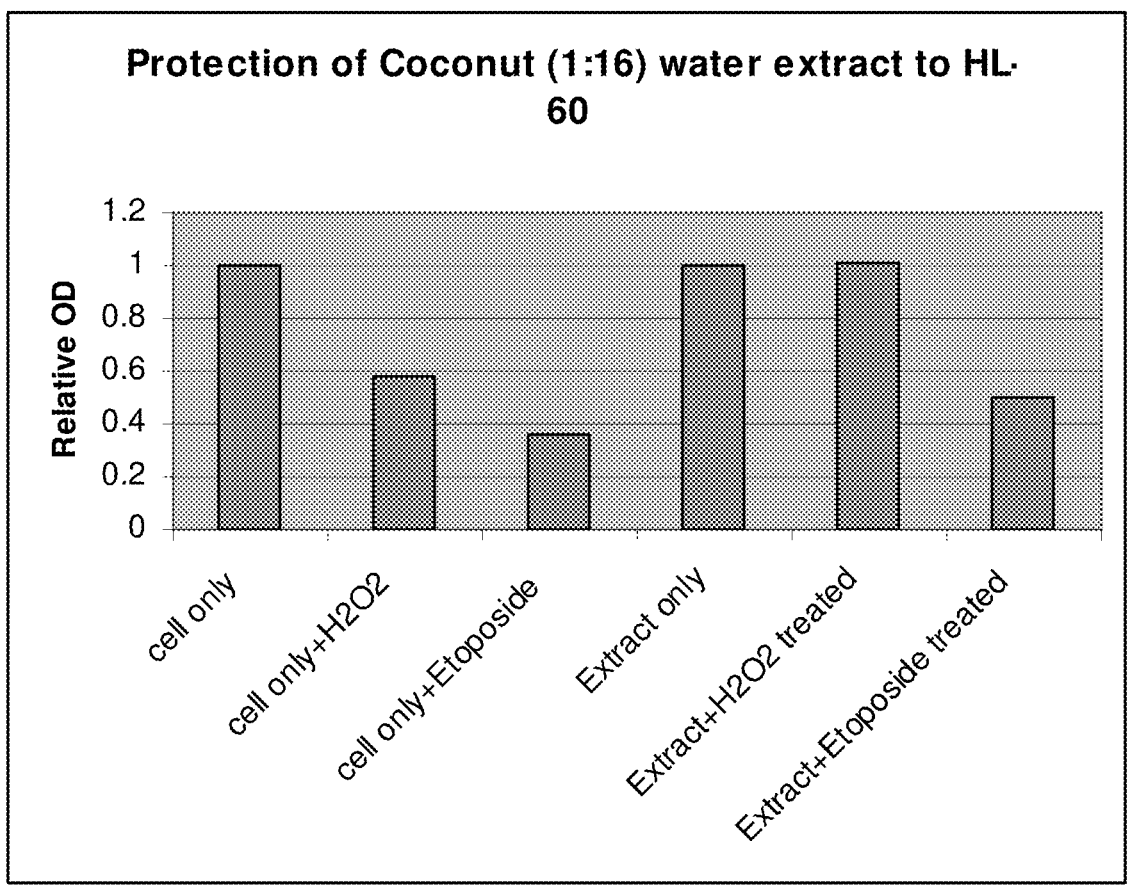
FIG. 3A depicts treatment of HL-60 cells in MTT assay with an extract based on coconut water having very potent cell protection activity as an unfermented "water" extract.

A detailed description of one or more embodiments of the invention is provided below along with accompanying tables and figures that illustrate the principles of the invention. As such this detailed description illustrates the invention by way of example and not by way of limitation. The description will clearly enable one skilled in the art to make and use the invention, and describes several embodiments, adaptations, variations and alternatives and uses of the invention, including what we presently believe is the best mode for carrying out the invention. It is to be clearly understood that routine variations and adaptations can be made to the invention as described, and such variations and adaptations squarely fall within the spirit and scope of the invention.

In other words, the invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims with or without some or all of these specific details.

A safe and effective pollen-based skin cream has been provided containing beeswax and optionally enzymes, which can be administered in a therapeutically effective amount to an individual for treatment of eczema or psoriasis. The pollen-based skin cream may be applied topically to the skin.

Pollen has a hard shell known as the sporopollenin which is very resistant to chemical degradation. Also on the surface of the pollen are proteins which cause known allergies. In one method a reaction is used to "explode" or "crack" the pollen grains under pressure (a commonly use abiotic approach) followed by use of a protease to hydrolyse and deactivate the allergy producing proteins. Optionally, a peptidase may then be used to create peptides from the soup or mixture created.

Instead of trying to explode the pollen grain (which did partially work), an attempt was made to manipulate or treat the pollen grains to begin germination and thus naturally release their contents thus optimizing the bioactivity and providing a far more targeted product. This may be considered a "biotic" approach to open the pollen. If the pollen grains are exploded then the compounds released are more in response to stress (which is good for some medical conditions), but if they are gently released through germination then they promote cell renewal and repair, as discussed previously. By using the biotic germination approach, the viable pollen grains began germinating whilst the damaged or dead pollen grains remained and could be filtered out. Thus this approach was also an improvement through removal of the dead pollen grains.

In one embodiment, it has been discovered that a two step process can be used to produce a pollen-based extract material, including opening and/or germinating pollen grains using a biotic method, and reacting the treated pollen grains with one or more beehive components, such as, for example, beeswax, propolis, etc.

Development of fermentation method and opening of pollen grains.

Initially, small amounts of dry pollen (25 g) were mixed with white sugar (5 g) and active yeast (5 g) in water (500 mL), inside of a sealed stainless steel bottle. At ambient temperature this mixture produced fermentation after about 72 hours, with production of alcohol and attendant alcoholic odor.

Follow on experiments performed with raw honey (Manuka, Rewa Rewa, clover) and honeydew from beech trees in Southern New Zealand (*Nothofagus* spp.) beech forests (isolated from the New Zealand beech scale insect *Ultracoelostoma assimile* (Maskell)). Within New Zealand this insect occurs mainly in South Island and is most common on black beech (*N. solandri solandri*) and mountain beech (*N. s. cliffortioides*), but generally any beech will suffice (Gaze, et al., N. Z. J. Ecol. (1983) 6:33-37). In these experiments the fermentation reaction occurred within about 24 hr at higher temperatures (37° C., 42° C., or 65° C.), while it took 48 hr at 25° C. It was shown that about 66% of the pollen grains open. Also, the use of honeydew did not produce an alcoholic odor, but instead a very golden yellow oily soup.

Analysis of fatty acid (FA) content was performed after fermentation and pollen grain opening, as shown in FIGS. 1 and 2 (NZLabs, Auckland, New Zealand). See also, Preparative examples A and B below for exemplary filtration of sediment after fermentation.

The results of the FA analyses indicates clearly that in the opened pollen grains the fatty acid content was preserved and protected. The key thing that this experiment demonstrated was that the fatty acids were released from the pollen, while in non-exploded pollen there were no fatty acids in the soup that was analyzed.

Development of Reaction Platform.

Once a way had been found to efficiently open pollen grains, reaction of the pollen grain contents and other components from the beehive (such as beeswax, propolis, etc.) was performed. The process was developed via several preparative examples as described below.

It was found that honeydew (from Southern Beech Forests) which contains insect enzymes worked better than raw honey. Honeydew is a substance that is defecated from scale insects on beech trees as they eat the sap. This honeydew is a honey substance but contains enzymes from the scale insects and their "gut microflora, including fructophilic lactic acid bacteria." This finding led to the conclusion that honeydew contains enzymes from the scale insect and from the various bacteria, which of course was also in certain raw honeys that were tested. Without being bound by theory, it is thought that the honeydew enzymes would be similar to the bee saliva and thus also aid in the second stage of the process.

Description of ingredients used in the representative two step process in various useful forms are as follows.

Raw pollen: contains fatty acids, polypeptides, EPA, DHA, long-chain alkanes, hormones, vitamins, phytohormones, cellulose, lignin, and flavanoids.

Raw beeswax: contains pheromones, phytic acid, chitin, and fatty acids.

Purified beeswax is available from Pure Nature Ltd. (Auckland, New Zealand). This material may be called pure or clean beeswax.

Raw honey: contains naturally occurring bacteria, such as lactic acid bacteria. Useful examples include Manuka, Rewa Rewa, clover, and the like.

Honeydew: contains potassium, sugars, insect enzymes and fructophilic lactic acid bacteria.

Pineapple powder: contains bromelain, a homologous serine protease, and peptidase enzymes; contains potassium.

Alternative plant powders containing flavanoids and/or enzymes: tamarillo (antioxidant and enzymes), blackcurrant (antioxidant/cellular repair/brain function), kawa kawa (bladder and digestive health/antioxidant/anti-inflammatory/detoxifying/acne), propolis (acne), pine bark (female hormone regulation and sunscreen), acai, pomengranate, cherry (sleep aid/melatonin), kiwifruit, paw paw, and feijoa. Freeze dried plant powders can be prepared as follows. A pulp of the desired plant is prepared, such as pineapple, tamarillo, kawa kawa, etc. The resulting pulp is frozen down to −20° C. over 48 hours and then freeze dried. Alternatively, useful freeze-dried plant powders are available from Alaron GMP Manufacturers (Alaron Products, Nelson, New Zealand). Alternatively, spray dried or even fresh plant sources can be used in the reaction, for example pineapple stem and fruit was originally used prior to access of freeze dried powders.

Other useful plant components may include, but are not limited to: apple flesh or skin; avocado pulp or skin; beech bark or leaves; blueberries, blackberries; acai berries, ginger; grape skin; hemp oil; rimu bark or leaves; turmeric; onion; orange; kiwifruit—flesh, skin, or seeds; kauri bark or leaves; kohe kohe; mango; manuka oil or leaves; noni; olives—waste, skin or oil; grape seed oil, argan oil, jojoba oil, and pohutakawa.

Coconut milk, i.e., Cononut water: contains hormones and nutrients. Coconut water/milk is obtained by buying fresh coconuts and draining the fresh milk just prior to use. Commercially available coconut milk can be used but cannot be pasteurized.

Coconut oil: contains polypeptides, fatty acids, EPA, DHA, and in particular myristic acid. One useful brand is Home Essentials brand, 100%.

Mussel oil: contains polypeptides, fatty acids, EPA, and DHA.

Certain beehive components, for example honey, honeydew, pollen, beeswax, raw propolis are sourced from Scott Apiaries, Trading as Hanmer Bees, Hanmer Springs, North Canterbury, New Zealand. Propolis can be prepared for use as a water extraction by treating 25 g propolis/50 mL water in a dark sealed glass vessel, with gentle rotation for 5 days at 28° C.

Glycerol (i.e., glycerine) is available from Sigma Aldrich (St. Louis, Miss.).

Water may be filtered, sterilized rain water, distilled water, deionized water, RO water, and the like.

Preparative Example A (including Pineapple powder)

The following ingredients were blended: raw pollen (50 g), raw beeswax (25 g), pineapple powder (12.5 g), raw honey (12.5 g), glycerol (12.5 g), and water (1000 mL). After blending the reaction mixture in a stainless steel container was heated to 60° C. and stirred for 15 min At this point the steel container was anaerobically sealed and pressurized to 120 psi. The container was stored at 60° C. for 24 hours. During this period pressure builds up in the container, and the mixture became bubbly and exothermic. Within 16 to 24 hours the reaction naturally stopped. The solution was then filtered to remove sediments. This reaction product extract was heated, poured into a cream formula (e.g., Ex. 3), and whipped using an egg beater manually until smooth (i.e. having a viscous even consistency).

This reaction resulted in a reaction product solution that still possessed protease activity, peptides and triglycerides.

In this manner the reaction product was formulated at 5 wt % in a commercially available aqueous cream (see, e.g., Experimental Aqueous Cream Formulation, Example 3). This formulated reaction product was trialled on subjects with various skin disorders. This reaction product worked on age spots, crusty eczema, psoriasis, herpes, corpus molluscum and acne. However, the reaction product caused irritation when used on inflamed eczema or lupus.

Preparative Example B (including Pineapple powder and Tamarillo powder)

The following ingredients were blended: raw pollen (50 g), raw beeswax (25 g), pineapple powder (6.25 g), tamarillo powder (6.25 g), mussel oil (25 g), honey (12.5 g), glycerol (12.5 g), and water (1000 mL). After blending the reaction mixture in a stainless steel container was heated to 60° C. and stirred for 15 min. At this point the steel container was anaerobically sealed and pressurized to 120 psi. The container was stored at 37° C. for 24 hours. During this period pressure builds up in the container, and the mixture became bubbly and exothermic. Within 16 to 24 hours the reaction naturally stopped. The solution was then filtered to remove sediments.

In this experiment the temperature was lowered to protect the plant powders. This process resulted in peptides, esterified fatty acids and esterified flavanoids. This lower temperature also protected the amino acids and vitamins from the pollen from heat denaturation. It is further contemplated that other oils may be used in place of mussel oil, including, but not limited to a combination of mussel oil/coconut oil (1:1 wt/wt).

To the extent the above reactions are producing and/or undergoing fermentation, the pollen-based material produced is considered to be fermentable.

In an embodiment, the pollen-opening fermentation reactions can be performed as described in a sealed steel container or other appropriate pressure vessel. In an alternative embodiment, the pollen-opening fermentation reactions can be performed as described aerobically in appropriate plastic or glass containers or reaction vessels.

One problem to this point was that all other competitors, and the process as described herein involved cracking open the pollen grain to release the contents within (an abiotic approach). What was most desired was a biotic method to produce those bioactive components in an enhanced state of bioactivity, as in when a pollen grain begins to germinate. At this point the contents are prepared during the osmosis process to be bio-available to optimal germination.

The plant cell germination process is equivalent to embryogenesis in humans and thus optimal for cell renewal, division, wound repair, etc.

Coconut milk (a.k.a. coconut water) is known to contain all the nutrients required for embryogenesis and the plant hormones including indoleacetic acid, gibberillin, and auxins, which stimulate cell division and growth. Coconut milk also contains potassium required for germination via osmosis. One study found that coconut milk (now known as coconut water) may be used to turn plant cells totipotent and to grow from a single cell into a whole new plant. This was carried out with the species lisianthus in which no one has previously been able to regenerate as it was recalcitrant to normal hormone stimulants (O'Brien, et al., *Plant Cell Tissue and Organ Culture* (1993) 33: 31-37).

Instead of cracking open the pollen grain, a biotic method is shown herein to trigger germinaton and thus activate it, that is produce enhanced bioactivity. Without being bound by theory, it is believed that if the pollen grain were germinated, then enzymes in honeydew and/or from the pollen itself can provide the protease/peptidase enzymatic reactions that other components could provide (e.g., Lactobacillus or pineapple powder).

Pollen grains will begin to germinate based on an osmotic uptake of potassium. If used in the reaction platform, honey/honeydew and pineapple all contain enough potassium to trigger this reaction, particularly at warmer temperatures. Coconut milk is also very high in potassium and thus the combination of the potassium with the phytohormones result in triggering germination.

By using the coconut water it incorporates into the product the minerals and growth hormones contained within the coconut water. These components work in synergy with the pollen to promote cell renewal and cellular repair, in contrast to the stressor effects of cracking or rupturing pollen.

The methods described above may be further understood in connection with the following Examples.

EXAMPLE 1

Reaction Platform

The following ingredients were blended: raw pollen (50 g), coconut milk (200 ml), and honeydew (12.5 g). These three ingredients were warmed to 30° C. and stirred for 30 minutes to stimulate germination. Next, the following ingredients were added: melted raw beeswax (25 g), glycerol (12.5 g), and water (1000 ml). Optional ingredients may include: coconut oil, pineapple powder, or other plant powders (as listed above). Depending on what components are added and the end desired medical or nutraceutical treatment the reaction is either carried out at 25° C., 30° C., 37° C., 42° C., or 65° C. The reaction platform can be carried out either anaerobically or aerobically.

EXAMPLE 2

Two Stage Reaction Platform

All reactions performed below are incubated anaerobically for 72 hours at 37° C. Optionally, beeswax may be used at 37° C. resulting in the reaction more anaerobic as it forms a solid wax layer over the other components. If this reaction is left for 7 days the beeswax is digested by the enzymes and becomes part of the solution (i.e., self-emulsifying).

EXAMPLE 2A

Eczema/Psoriasis

| Ingredient | Weight (g) |
|---|---|
| Pollen | 50 g |
| Beeswax | 25 g |
| Coconut Oil | 25 g |
| Glycerol | 12.5 g |
| Honeydew | 12.5 g |
| Coconut Water | 200 ml |

(Stage 1) Pollen was soaked in coconut water for 30 minutes at 25° C. Concurrently the beeswax was melted in a stainless steel bowl, which is sitting in boiling water. Once the beeswax was melted it was stirred vigorously for 5 minutes, and the bowl placed into the incubator at 65° C. resulting in the beeswax remaining liquid.

After 60 minutes soaking, glycerol was then stirred into the pollen mixture, followed by the honeydew. This mixture is then stirred for 30 minutes at 25° C., which completed part 1. Next, the coconut oil was stirred into the melted beeswax, which completed part 2.

The pollen mixture (part 1) was then stirred into the beeswax mixture (part 2) and the whole mixture stirred vigorously by hand for about 15 minutes until a thick jelly formed (Stage 1 ends). It is noted that stirring by hand was laborious and that magnetic stirring on a hot plate would be useful.

(Stage 2) This jelly mixture was then placed into a stainless steel container with a screw sealable lid, and incubated at 37° C. for a minimum of 72 hours, which produced the isolated 2-stage extract (Stage 2 ends).

In a preferred embodiment, plant powders (or other useful plant parts) such as tamarillo, kawa kawa, and the like, may be added after the jelly is formed, then the whole mixture subjected to heating under sealed conditions and/or fermentation. In an alternative embodiment, after the jelly is formed, if any other components such as, for example, pineapple powder, fruit powder, etc. are required, these are added as the mixture cools. That is, tamarillo, kawa kawa, etc. can be added after the end of Stage 2.

In a further embodiment, other components such as, for example, pineapple powder, tamarillo, kawa kawa, fruit powder, etc. may be added after the end of Stage 2 and heated.

It is understood that the stage 2 fermentation process can be carried out in a range from about 24 hours to 168 hours. In one preferred embodiment, incubation is carried out at 37° C. for about 24 hrs to 72 hrs. In a more preferred embodiment, incubation is carried out at 37° C. for about 72 hrs.

In another alternative embodiment, increases in coconut water content of stage 1 can reduce manufacturing costs.

In another alternative embodiment, the melted beeswax (or part 2 component) can be maintained at lower temperatures (e.g., 42° C., or 37° C.) in order to preserve other more sensitive components (such as amino acids, peptides, or fatty acids). In this embodiment, the beeswax self-emulsifies into the final product mixture.

EXAMPLE 2B

Age Spots/Actinic Keratosis

| Ingredient | Weight (g) |
| --- | --- |
| Pollen | 50 g |
| Beeswax | 25 g |
| Coconut Oil | 25 g |
| Glycerol | 12.5 g |
| Honeydew | 12.5 g |
| Coconut Water | 200 ml |
| Pineapple powder | 12.5 g |

EXAMPLE 2C

Antimicrobial and Wound Healing

| Ingredient | Weight (g) |
| --- | --- |
| Pollen | 50 g |
| Beeswax | 25 g |
| Coconut Oil | 25 g |
| Glycerol | 12.5 g |
| Honeydew | 12.5 g |
| Coconut Water | 200 ml |
| Propolis | 5 ml* |

*Added at the end of the reaction. Propolis is prepared as 25 g/50 ml water.

EXAMPLE 2D

Anti-Viral—Herpes, Shingles, Corpus Molluscum, Chicken Pox

| Ingredient | Weight (g) |
| --- | --- |
| Pollen | 50 g |
| Beeswax | 25 g |
| Coconut Oil | 25 g |
| Glycerol | 12.5 g |
| Honeydew | 12.5 g |
| Coconut Water | 200 ml |
| Kawa Kawa powder | 12.5 g |
| Propolis | 5 ml* |

*Added at the end of the reaction. Propolis is prepared as 25 g/50 ml water.

In following examples 2E, 2F and 2G beeswax is omitted, so the solution is more liquid (less viscous) upon addition of the oil, and the reaction takes another 24-48 hours to complete.

EXAMPLE 2E

Cosmetic—Beauty/Anti-Aging

| Ingredient | Weight (g) |
| --- | --- |
| Pollen | 50 g |
| Coconut Oil | 25 g |
| Glycerol | 12.5 g |
| Honeydew | 12.5 g |
| Coconut Water | 180 ml |
| Algae water | 20 ml* |

*Micro algae is grown to an exponential phase, centrifuged and slurry added to reaction vessel just prior to fermentation at 30° C.

Optionally, 12.5 g blackcurrant powder is added to this example as an antioxidant.

EXAMPLE 2F

Core Formula—Optional Tamarillo

| Ingredient | Weight (g) |
| --- | --- |
| Pollen | 50 g |
| Coconut Oil | 25 g |
| Glycerol | 12.5 g |
| Honeydew | 12.5 g |
| Coconut Water | 200 ml |
| Tamarillo powder (optional) | 12.5 g |

EXAMPLE 2G

Cosmetic—Beauty/Female Hormonal

| Ingredient | Weight (g) |
| --- | --- |
| Pollen | 50 g |
| Coconut Oil | 25 g |
| Glycerol | 12.5 g |
| Honeydew | 12.5 g |

-continued

| Ingredient | Weight (g) |
| --- | --- |
| Coconut Water | 180 ml |
| Algae water | 20 ml* |
| Pine bark powder [a] | 12.5 g |

*Micro algae is grown to an exponential phase, centrifuged and slurry added.
[a] Pine bark powder is prepared by hot water extraction of pine bark, then freeze drying.

Chemical Analysis

Reaction samples made in accordance with the principles of the invention, namely Example 2A or 2B, were analyzed to assess how the chemical components in these mixtures changed during incubation. Phytochemical analysis was performed by liquid chromatograph-high resolution mass spectrometry (LC-HRMS), and the protein/peptide composition was assessed by SDS acrylamide gel electrophoresis (SDS-PAGE), using standard methods.

After 0 hrs (starting material) to 72 hrs of incubation in the stage 2 fermentation reaction, the samples were thoroughly mixed and a portion (1.0-1.5 g) extracted with ethanol. Pineapple powder was added to starting material DE5 and DE7 (Ex. 2A with or without beeswax, respectively) after time 0 for incubation in accordance with Example 2B. The resulting extracts were analyzed by LC-MS using reversed-phase ultra-high performance liquid chromatography (RP-UHPLC) and negative ion electrospray ionization (ESI).

Now referring to FIG. 5, the samples tested were as follows:

DE2: Extract sample 2A, without beeswax, 72 hrs
DE3: Extract sample 2A, 72 hrs
DE4: Extract sample 2B, without beeswax, 24 hrs
DE5: Extract sample 2A, 0 hrs (starting material—Stage 1)
DE6: Extract sample 2B, 24 hrs
DE7: Extract sample 2A, without beeswax, 0 hrs (starting material—Stage 1)
DE8: Extract sample 2B, without beeswax, 72 hrs
DE9: Extract sample 2B, 72 hrs A 12.5% reduced SDS-PAGE gel was used. The markers were Biorad #161-0373, stain type: All Blue (Bio-Rad Lab., Hercules, Calif.).

Figure 5:
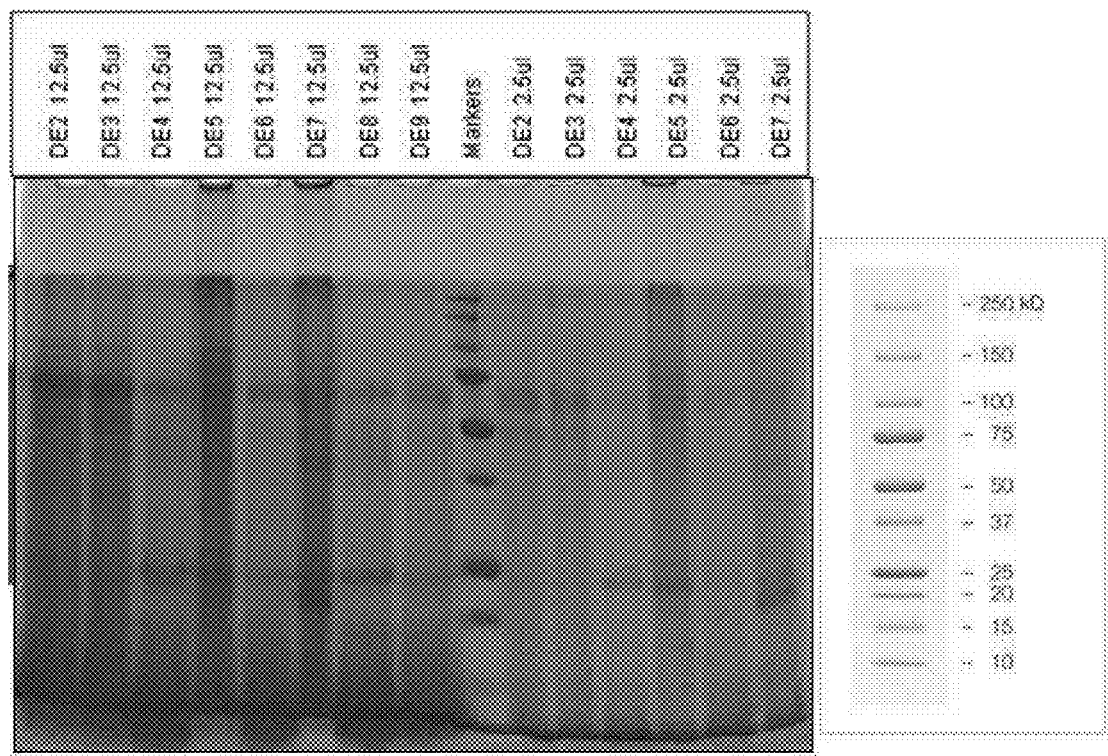
FIG. 5 depicts gel electrophoresis (SDS-PAGE) analysis of the opened and fermented pollen prepared according to an embodiment of the present invention. Lane markings are as follows: DE2-DE9 (12.5 µl loading), protein Markers, and DE2-DE7 (2.5 µl) loading, as described below.

Generally, FIG. 5 shows that the larger molecular weight proteins were degraded or digested into smaller molecular weight protein components as part of the 2-stage process.

Samples DE5 and DE7 were the (stage 1) starting materials for the 2-stage process and showed that a significant amount of protein in the sample was of a large molecular weight (>250 kD)—so much so that much of it did not enter the gel. Samples DE2 and DE3 showed a significant band between 50 and 75 kD (which was also present in lesser amounts in the remaining samples). Another band at about 25 kD appeared in samples DE4, DE6 and DE8, and to a lesser extent in DE9.

Samples DE4, DE6 and DE8 showed significant staining at molecular weights less than 151(D. Samples DE2, DE3 and DE9 showed protein/peptides to a lesser extent in this range.

Thus, the size profile of proteins in the incubated samples over time is overtly smaller compared to the starting material (DE5 and DE7), either with or without pineapple powder enzymes, or with or without beeswax.

Figure 6:
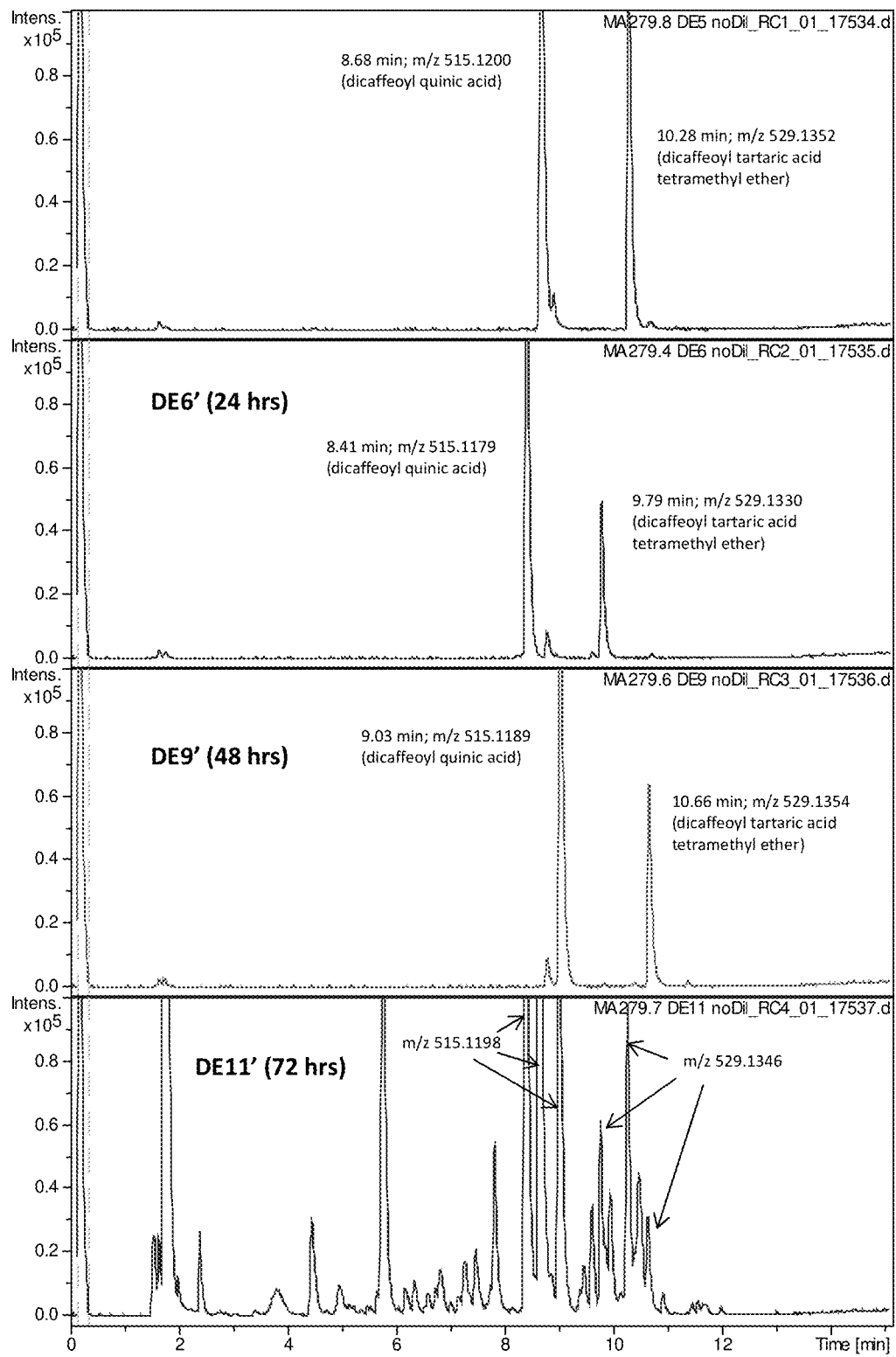
FIG. 6 depicts RP-UHPLC and negative ion electrospray ionization (ESI) analysis of the opened and fermented pollen prepared according to an embodiment of the present invention (Example 2A), showing products of the stage 2 fermentation reaction up to 72 hrs.
Figure 7A:
FIG. 7A shows a photograph of a hand of a human patient having severe eczema before treatment, with the white label containing the text: DEC/1200 #1 Right Hand, 1009/DMZ, 3 Mar. 2014 V2.
Figure 7B:
FIG. 7B shows a photograph of the eczema patient of FIG. 7A after 4 weeks of topical treatment using a fermented pollen-based cream of Example 6B, with the white label containing the text: DEC/1200, #1 Right Hand, 1009/DMZ 1 Apr. 2014 V5.
Figure 8A:
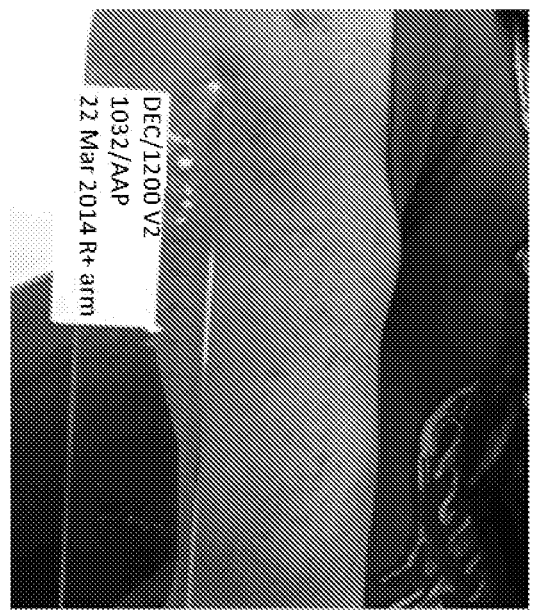
FIG. 8A shows a photograph of an arm of a human patient having severe eczema before treatment, with the white label containing the text: DEC/1200, V2, 1032/AAP, 22 Mar. 2014, R+ arm.
Figure 8B:
FIG. 8B shows a photograph of the eczema patient of FIG. 8A after 4 weeks of topical treatment using a fermented pollen-based cream of Example 6B, with the white label containing the text: DEC/1200, R+ arm, 1032/AAP, V5, Apr. 22, 2014.

Turning now to FIG. 6, the progression of the stage 2 incubation was observed and analyzed for reaction products. The samples tested were as follows:

DE5: Extract sample 2A, 0 hrs (starting material—Stage 1), as above
DE6': Extract sample 2A, 24 hrs
DE9': Extract sample 2A, 48 hrs
DE11': Extract sample 2A, 72 hrs The progression of the stage 2 fermentation reaction showed a pattern of compounds that were determined to be dicaffeoyl quinic acid isomers, and, it is believed, dicaffeoyl tartaric acid ester or ether compounds. As shown in FIG. 6, after 72 hours, it was observed that multiple isomers of the phenolic compound dicaffeoyl quinic acid had formed, which is an indicator or marker of the 2-stage reaction. It is believed that multiple dicaffeoyl tartaric acid ester or ether isomers formed as well (e.g., a tetramethyl ether of the caffeoyl portions). These samples have been shown to contain substantial amounts of the caffeoyl quinic acid isomers, and, it is believed, dicaffeoyl tartaric acid ester or ether compounds (i.e., chicoric acid derivatives, including methyl ethers or esters).

Thus, while not intended to be bound by theory, peptides are created in the 2-stage method according to a process of "lipophilization" or "lipolyzation" in which protein is digested, phenolic compounds are isomerized or methylated, and fatty acids may be involved in esterification reactions to produce useful and beneficial new products. In another embodiment, it is expected that hydroxylation and/or acetylation of flavonoids may occur in conjunction with fatty acids. In another embodiment, it is expected that hydrolysis of tannins, or glycosylation of aglycones may occur during the 2-stage fermentation reaction. In yet another embodiment, it is expected that hydroxylation of fatty acids may occur during the 2-stage fermentation reaction. In fact, the lipid composition of the 2-stage reaction product produced increased lipid content as observed by HPLC analysis.

An emollient cream was developed as follows.

EXAMPLE 3

Experimental Aqueous Cream Formulation

| Ingredient | Wt/Wt (%) |
| --- | --- |
| Cetostearyl Alcohol | 8.1% |
| White soft paraffin | 15.0% |
| Liquid paraffin | 6.0% |
| Sodium Lauryl Sulfate | 0.9% |
| Phenoxyethanol | 1.0% |
| Purified Water | 70.0% |

Aqueous cream without the extracts added was used as the placebo, thus the prerequisite was that the addition of the extract had to be clinically significantly better than the aqueous cream which is the current non-steroidal anti-eczema treatment.

Accordingly, the use of parabens significantly inhibited efficacy of the extract in several human volunteers. Phenoxyethanol did not fully inhibit but still reduced efficacy extract in several human volunteers, which was hypothesized as due to the bacteriocidal properties. Similar results to parabens were found with methyl parahydroxybenzoate, i.e. efficacy of the extract was significantly reduced.

Next, a batch of aqueous cream and was prepared using Geogard 221, a bacteriostatic preservative as a replacement for phenoxyethanol and/or parabens, containing dehydroacetic acid 8%, benzyl alcohol 87% (available from Lonza, Allendale, N.J.). This formulation provided full efficacy of the extract when tested in several human volunteers. Thus, the type of preservative was found to be important, arguably an additive having more "natural product" similarity.

EXAMPLE 4

Natural Base Cream Formulation

| Ingredient | Wt/Wt (%) |
|---|---|
| Cetostearyl Alcohol | 8.1% |
| Cetomacrogol* | 15.0% |
| Glycerine | 2.5% |
| Crodamol (coconut oil) | 2.0% |
| Beeswax | 2.0% |
| Geogard** | 0.5% |
| Purified Water | 70.0% |

*Cetomacrogol 1000, a PEG polymer
**Geogard 221

Thus, a useful aqueous cream formulation was discovered that is very stable and uses no bacteriocidal preservatives. This material is a beautiful soft cream that may be applied to human skin.

To the base cream of Example 4 was added the two-stage extract of Example 2A in an amount of 5% by wt. based on the total weight of the formulation. Useful amounts of the two-stage extract can range from about 0.5% by wt. to about 10% by wt. based on the total weight of the formulation. A preferred range of the two-stage extract can range from about 0.5% by wt. to about 5% by wt. based on the total weight of the formulation.

In addition, essential oil or fragrance was added to the base cream of Example 4, in that tangerine oil extract was added in an amount of 0.4% by wt. based on the total weight of the formulation. Useful amounts of one or more essential oils can range from about 0.4% by wt. to about 1% by wt. based on the total weight of the formulation.

EXAMPLE 5

Testing of Base Cream Including Example 2A Extract

The base cream of Example 4 including 5 wt % Example 2A extract and 0.4 wt % tangerine oil extract was tested as follows using human volunteers (Table 1).

TABLE 1

| Subject No. | Sex | Age | Skin/ Inflammatory Condition | Result |
|---|---|---|---|---|
| 1 | M | 51 | psoriasis on limbs | redness and scaly skin cleared within 5 days |
| 2 | F | 6 | corpus molluscum | skin cleared within 4 days |
| 3 | F | 48 | lupus | history of steroids, showed reduced flare ups and severity |
| 4 | F | 35 | lupus | history of steroids, showed reduced flare ups and severity |
| 5 | F | 22 | lupus | used instead of steroids, redness reduced, no need for steroids |
| 6 | F | 58 | eczema | over 4 days itching, redness and infection cleared |

TABLE 1-continued

| Subject No. | Sex | Age | Skin/ Inflammatory Condition | Result |
|---|---|---|---|---|
| 7 | M | 65 | agespots, solar keratosis | over 2 weeks crusted and exfoliated off |
| 8 | F | 15 | eczema | over 4 days itching, redness and infection cleared |
| 9 | F | 23 | eczema | over 4 days itching, redness and infection cleared |
| 10 | M | 45 | eczema | over 4 days itching, redness and infection cleared |
| 11 | M | 28 | eczema | over 4 days itching, redness and infection cleared |
| 12 | F | 33 | eczema | over 4 days itching, redness and infection cleared |
| 13 | F | 16 | eczema | over 4 days itching, redness and infection cleared |
| 14 | F | 42 | eczema | over 4 days itching, redness and infection cleared |
| 15 | M | 58 | psoriasis | redness and scaly skin reduced |
| 16 | M | 22 | psoriasis | redness and scaly skin reduced |
| 17 | F | 17 | psoriasis | redness and scaly skin reduced |
| 18 | M | 51 | athletes foot/ jock itch | fungal infection clears |

As shown in Table 1, this formulation cleared the eczema and psoriasis on the volunteers. Subjects 1, 3, 4, 5, 8, 9 and 10 spent a week with no cream and then trialled Example 6 cream (below) prepared for the clinical trial with equivalent results to Example 4.

EXAMPLE 6A

Skin Cream Formulation

A skin cream formulation was prepared as follows.

| Ingredient | Wt (%) |
|---|---|
| Olivem 1000 ECO CERT (Cetearyl Olivate & Sorbitan Olivate) | 7 |
| Shea Butter Organic | 2 |
| Macadamia Nut Oil Organic | 4 |
| Myristyl Myristate | 2 |
| Safflower Oil Organic | 4 |
| Glycerine | 2 |
| Geogard** | 1 |
| Vitamin E | 2 |
| 2-Stage Extract (Example 2A) | 5 |
| Tangerine Fragrance (tangerine oil extract) | 1 |
| Deionized Water | 70 |

**Geogard 221

Olivem 1000, available from B&T Srl (Milan, Italy), is a nonionic, non-ethoxylated self-emulsifying system derived from olive oil for oil-in-water creams and lotions.

Initial testing using Example 6A in human volunteers as in Example 5 gave similar results with respect to eczema and psoriasis, etc.

EXAMPLE 6B

Skin Cream Formulation

In a further embodiment, a skin cream formulation was prepared.

| Ingredient | Wt (%) |
| --- | --- |
| Olivem 1000 ECO CERT (Cetearyl Olivate & Sorbitan Olivate) | 7 |
| Shea Butter Organic | 2 |
| 2-Stage Extract (Example 2A) [1] | 10 |
| Safflower Oil Organic | 3 |
| Macadamia Nut Oil Organic | 2 |
| Deionized Water | 70 |
| Glycerine | 2 |
| Geogard 221 | 1 |
| Vitamin E | 2 |
| Tangerine Fragrance (tangerine essential oil) | 1 |

[1] lipolyzed fatty acid and peptides, as shown in FIGS. 1, 2 and 5 as described herein.

The final formulation is an off-white viscous cream, pH 4.0-5.0. Microbiological properties: aerobic plate count: (30° C.) 377 cfu/g; yeast and mold: <1 cfu/g. The cream may be applied topically by hand to a human skin surface.

In an embodiment, the 2-stage extract may be used in a range of from about 1% by weight to about 10% by weight. In another embodiment, water may be used in a range of from about 70% by weight to about 90% by weight. Increases in water content, and/or alternatively, increases in coconut water content of stage 1 (as discussed above) can reduce manufacturing costs.

The cream formulation of Example 6B was tested in a clinical trial as follows.

EXAMPLE 6C

Clinical Study—Eczema

The purpose of this study was to determine the effectiveness of Example 6B in the treatment of mild to moderate eczema, including reducing the appearance of lesions, reducing the symptoms of itching and scaling, and reducing redness.

Clinical Study Design

This study was designed as an open-label, adaptive-design pilot study.

Otherwise healthy subjects, 18-70 years of age, with mild to moderate eczema were included in the study. A total of n=40 subjects were screened, and from this, n=21 were randomized; however, only n=20 subjects completed the study. Other standard inclusion/exclusion criteria were used. Adverse events were monitored. Initial IRB approval of the protocol was granted by the MaGil IRB (Rockville, Md.). All recruitment materials were approved by the IRB prior to use.

The study duration was up to 5 weeks for each subject comprising 5 visits, with the testing phase being 30 days (approx. 4 weeks).

V1: Screening Visit—Day -7
V2: Day 0—Baseline
V3: Day 7
V4: Day 15
V5: Day 30—End of Study Subjects were required to undergo a 7-day washout of any and all treatments for eczema.

Dermatologic Assessments. Dermatologic examinations by a qualified practitioner were performed. This assessment includes the Severity Scoring of Atopic Dermatitis (SCORAD) an evaluation and grading of lesion quality. Subjects completed the Dermatologic Life Quality Index (DLQI), a self-assessment on each subject's own skin condition.

Photographs. Subjects were photographed to examine and evaluate skin lesion(s), which were identified by anatomical location and size.

Dispensing Procedures. The following were dispensed at this visit:

Subjects were given a one-week supply of study product (Example 6B cream) and instruct to apply it twice a day. Subjects were given a daily dosing diary.

Instruction: Patients were instructed to apply the cream topically to the affected area(s) twice per day. That is, patients with eczema were instructed to apply the cream topically to a given lesion twice per day.

Dosages: Based on the clinical trial presented herein, average Example 6B cream use per day, per patient was 2.46 g. Average Example 6B cream use per lesion was 1.52 g.

Data Analysis. Statistical Software for Social Sciences (SPSS version 19) was used to run all descriptive and inferential analyses for all endpoints.

The primary objective was to assess the reduction in the appearance of lesions by examining skin lesion photographs (FIGS. 7A-7B and 8A-8B). The second objective was to assess the reduction in the symptoms of itching, scaling, and redness via different dermatologic assessments, as shown in Table 1A.

TABLE 1A

| Endpoint | Visit/Day | Change | Significance | P-value |
| --- | --- | --- | --- | --- |
| Severity of Eczema | Baseline vs. Visit 5 (Day 30) | Decreased overall lesions | Yes | 0.001 |
| VAS SYMPTOM SCORE (ITCHING) | Week 1 vs. Week 2 | Decreased from Baseline | Yes | 0.001 |
| | Week 1 vs. Week 3 | Decreased from Baseline | Yes | 0.011 |
| | Week 1 vs. Week 4 | Decreased from Baseline | Yes | 0.031 |
| VAS SYMPTOM SCORE (SCALING) | Week 1 vs. Week 2 | Decreased from Baseline | Yes | 0.0001 |
| | Week 1 vs. Week 3 | Decreased from Baseline | Yes | 0.003 |
| | Week 1 vs. Week 4 | Decreased from Baseline | Yes | 0.031 |
| VAS SYMPTOM SCORE (REDNESS) | Week 1 vs. Week 2 | Decreased from Baseline | Yes | 0.005 |
| | Week 1 vs. Week 3 | Decreased from Baseline | Yes | 0.001 |
| | Week 1 vs. Week 4 | Decreased from Baseline | Yes | 0.043 |

TABLE 1A-continued

| Endpoint | Visit/Day | Change | Significance | P-value |
|---|---|---|---|---|
| SCORAD INDEX | Baseline vs. Visit 3 (Day 7) | Decreased from Baseline | Yes | 0.049 |
| | Baseline vs. Visit 5 (Day 30) | Decreased from Baseline | Yes | 0.004 |
| Dermatologic Life Quality Index (DLQI) | Baseline vs. Visit 5 (Day 30) | Decreased from Baseline | Yes | 0.031 |
| VITALS (Weight) | Baseline vs. Visit 5 (Day 30) | Increased from Baseline | Yes | 0.032 |

Visual analogue scale (VAS) Symptom Score for Itching, Scaling, and Redness. Subjects were also required to undergo Dermatologic Assessment for Itching, Scaling and Redness of the Eczema Skin Lesions. Analyses revealed significant decreases in the Average VAS Symptom Score for Itching, Scaling, and Redness from Week 1 to Weeks 2, 3, and 4 (p-value≤0.05, for all time points).

In accordance with Table 1A, Itching (VAS) Symptom Score was reduced −30.27% from baseline from week 1 to week 4.

In accordance with Table 1A, Scaling (VAS) Symptom Score was reduced −30.53% from baseline from week 1 to week 4.

In accordance with Table 1A, Redness (VAS) Symptom Score was reduced −33.95% from baseline from week 1 to week 4.

Severity of Eczema was found to have statistically significant changes from Baseline to Day 30 (p-value≤0.05). Overall, moderate eczema was reported to decrease in severity and 19.44% lesions had disappeared by Day 30. It is noted that the majority of the moderate to severe lesions were also reduced (based on a count of lesions, and also assessment of type: mild, moderate, or severe). See Table 1A.

It was also observed that the overall average size (length X width) of the eczema skin lesions decreased substantially upon treatment with the topical cream. For example, average length was reduced −23.8% (from 6.3 cm to 4.8 cm), while average width was reduced −22.8% (from 3.9 cm to 3.0 cm).

SCORAD is a clinical tool used to assess the extent and severity of eczema (Scoring Atopic Dermatitis). Dermatologists may use this tool before and after treatment to determine whether the treatment has been effective.

The Severity Scoring of Atopic Dermatitis (SCORAD) index was used as the standardized ratings scale for eczema. This composite scoring index was developed by the European Task Force on Atopic Dermatitis in 1993. It has undergone testing for validity and reliability and has shown sensitivity change in trials of topical steroids and UV-A therapy. It combines an assessment of disease extent using the rule of nines with 6 clinical features of disease intensity (assessed at a single representative site), plus a visual analogue score for itch and sleep loss. The index has shown agreement with global assessments of disease severity as well as with various circulatory factors thought to reflect disease activity in atopic dermatitis.

Figure 10:
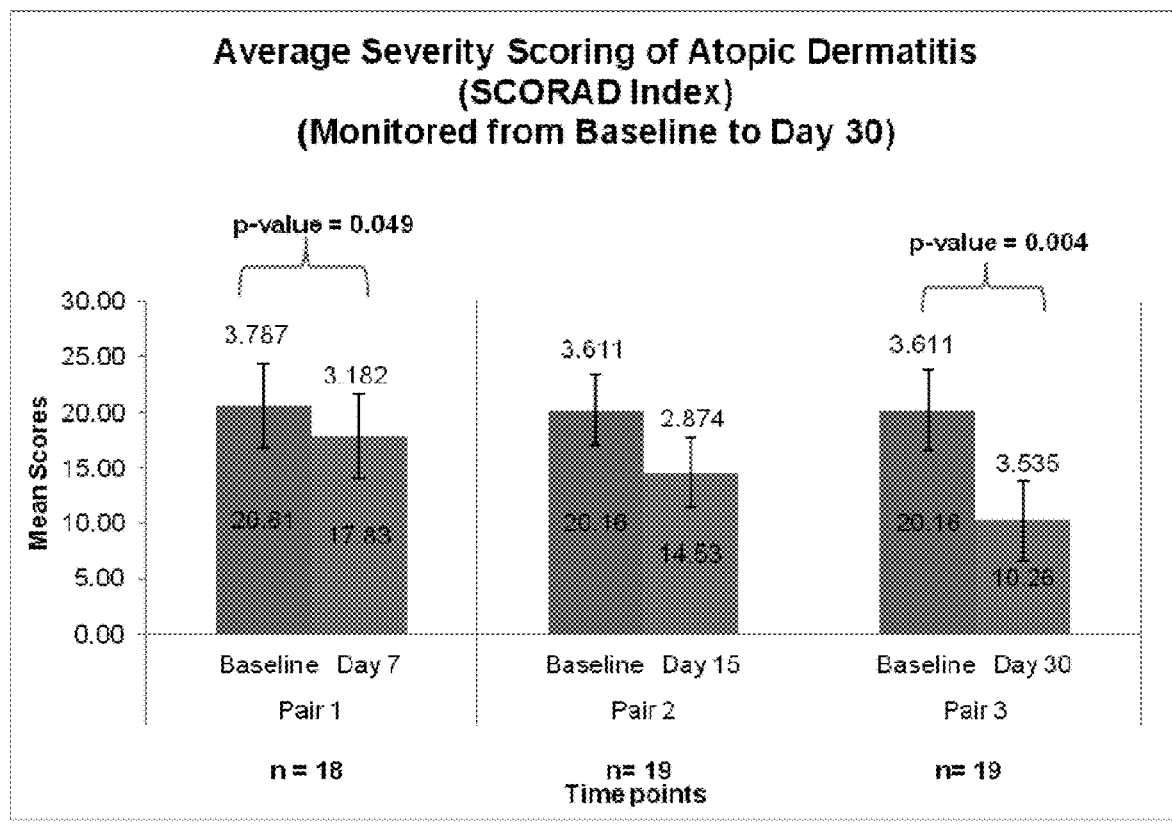
FIG. 10 depicts a bar graph showing Severity Scoring of Atopic Dermatitis (SCORAD) index for a clinical treatment group (n=20) receiving a skin cream (Example 6B) containing fermented pollen-based extract prepared according to an embodiment of the present invention.

In accordance with Table 1A, within-subject analyses showed that subjects in the treatment group had statistically significant decreases in the average SCORAD index score from baseline to Day 7 (p-value=0.049) and Day 30 (p-value=0.004). Moreover, consistent decreases from Baseline to all time points were noted and the largest decrease was found at Day 30 (−49.11%). FIG. 10 shows the SCORAD results.

Subjects completed the Dermatologic Life Quality Index (DLQI), a self-assessment on each subject's own skin condition. Dermatology Life Quality Index (DLQI) consists of 10 questions concerning patients' perception of the impact of skin diseases on different aspects of their health related quality of life over the last week.

Figure 11:
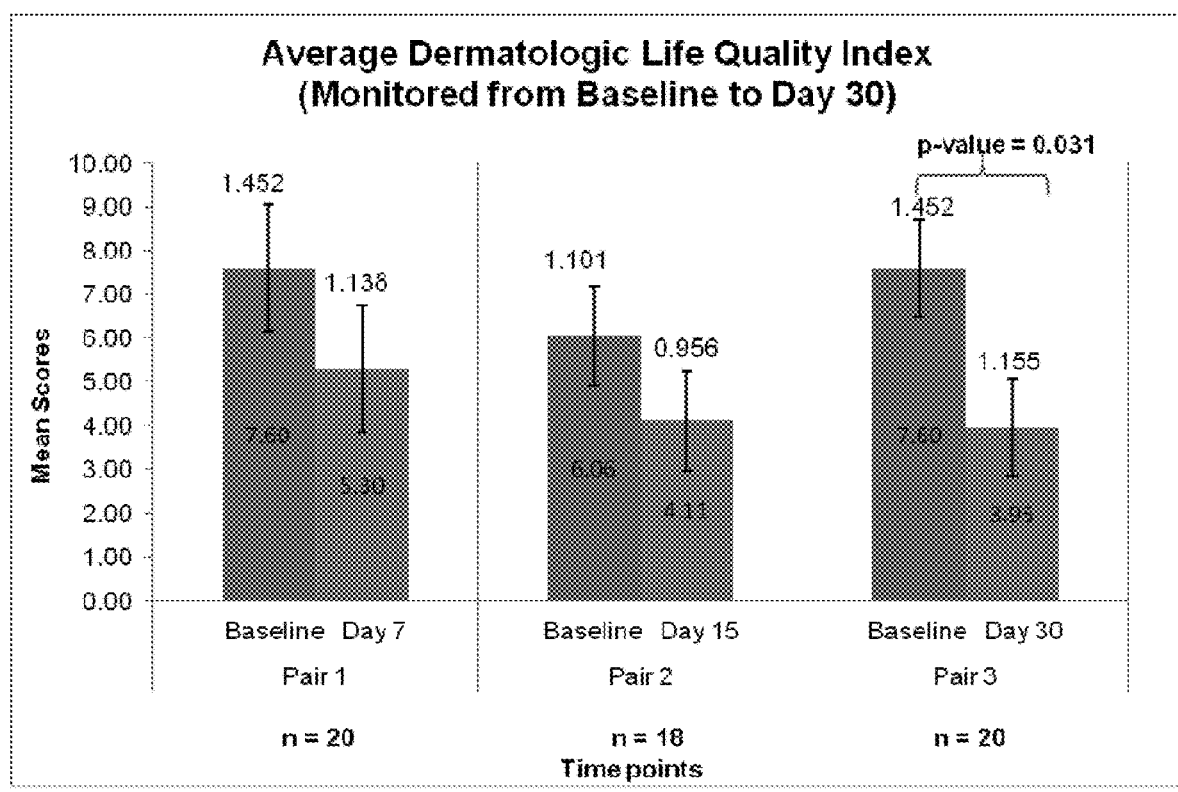
FIG. 11 depicts a bar graph showing Dermatology Life Quality Index (DLQI) for a clinical treatment group (n=20) receiving a skin cream (Example 6B) containing fermented pollen-based extract prepared according to an embodiment of the present invention.

In accordance with Table 1A, the Average Dermatology Life Quality Index (DLQI) scores of the subjects were shown to have constant decreases from baseline to all time points, with the largest decrease at Day 30 (−48.03%). Statistically significant changes were observed from baseline to Day 30 (p-value≤0.05). FIG. 11 shows the DLQI results.

The vital scores of the subjects were also assessed from Day 0 to Day 30. It was observed that the subjects had no statistically significant changes in their Body Temperature, Systolic Blood Pressure, Diastolic Blood Pressure, Pulse Rate, and Respiratory Rate from baseline to any time point despite exhibiting either an increasing or decreasing trend. On the other hand, significant but minor increase in Weight was observed from baseline to Day 15 (p≤0.05). In accordance with Table 1A, on Day 15 weight increased +0.81% (about 1.2 lbs), and by Day 30, weight increased +0.97% (about 1.5 lbs) respectively, compared to baseline. This result could be valuable from a nutritional standpoint for patients suffering from various conditions or diseases as described herein.

There were no adverse events or serious adverse events reported for this study.

In conclusion, the results of the clinical study indicated that product Example 6B was effective in treating mild to moderate atopic dermatitis, also known as eczema, as demonstrated by the reduction in the size of skin lesions along with other hallmarks of the disease such as itching, scaling and redness.

It is expected that the skin cream will successfully treat symptoms associated with eczema, psoriasis, and related inflammatory conditions when applied topically. The cream is generally applied topically to the skin in a manner substantially covering the affected surface area. The cream may be formulated as a cosmetic, pharmaceutical, or nutraceutical composition, including a pharmaceutically or nutraceutically acceptable carrier, respectively.

Useful therapeutic dosages of the skin cream (Example 6B) can range, but are not limited to, from about 1 g to about 5 g in a human individual. Another narrower suitable dose range is from about 1 g to about 2 g, for example, 1-2 g/lesion. Another useful therapeutic dosage for application to human skin is from about 0.5 g/lesion to about 1.5 g/lesion.

The skin cream (Examples 6A-6D) can be provided in daily dosages of from about 1 g to about 5 g, in a human patient, for example. Another narrower suitable dosage range is from about 1 g to about 2 g daily. Another narrower suitable dosage range is from about 1 g to about 3 g daily.

EXAMPLE 6D

Psoriasis

A test cream of was prepared by substituting the 2-Stage Extract (Example 2B) for Extract 2A in Example 6C.

Figure 9A:
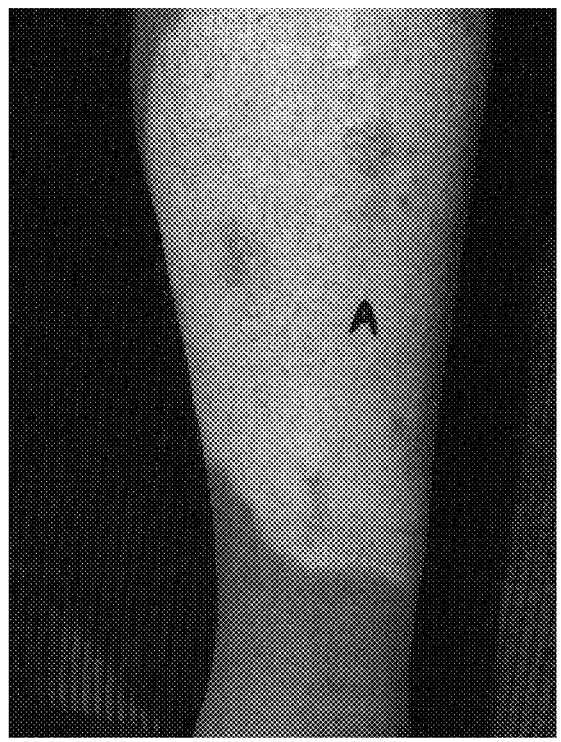
FIG. 9A shows a photograph of a leg of a human patient having psoriatic lesions before treatment.
Figure 9B:
FIG. 9B shows a photograph of the psoriasis patient of FIG. 9A after 4 weeks of topical treatment using a fermented pollen-based cream of Example 6D.

A psoriasis patient having scaly outbreaks on a leg (FIG. 9A) was treated with the psioriasis test cream. Topical application of the cream (as shown above in Example 6C) over 4 weeks provided a noticeable improvement by reducing encrustation and scaling. (FIG. 9B).

It is further contemplated that the 2-Stage reaction platform as described herein can be used to produce oral formulations of pollen-based reaction products in combination with the components of beehives. Such products may include a 2-stage reaction mixture which has been freeze dried or lyophilized, then appropriately formulated for oral administration.

EXAMPLE 7

Cell Protection Assay

The MTT assay has been adapted to measure whether an extract could protect the cells from apoptosis (programmed cell death) either by:
1. Oxidative stress using hydrogen peroxide, or
2. DNA damage using etoposide (chemotherapy drug).

The MTT assay is traditionally used to measure the cytotoxicity of a compound/extract. This is done by measuring cell proliferation of the cells by the reduction of MTT (3-(4,5-dimethylthiazol-2-yl)-2,5-diphenyltetrazolium bromide) to formazan in the mitochondria of living cells. If the cells are stressed or dying they cannot carry out this reaction and thus OD (optical density) is low. If the cells are functioning well in the presence of the extract then cell proliferation occurs. Therefore OD directly relates to the number of viable (living) cells.

Figure 3B:
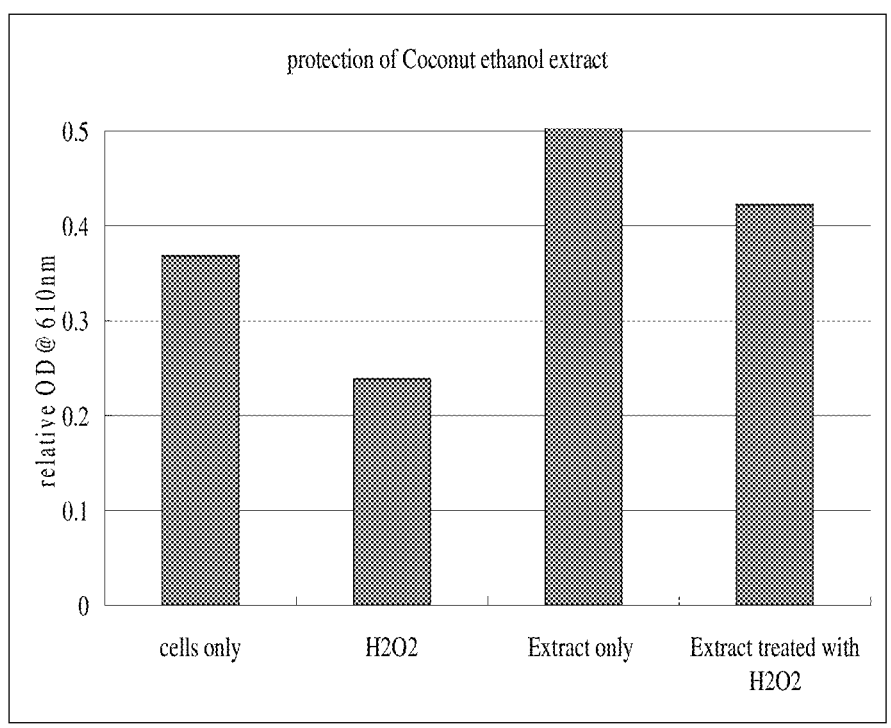
FIG. 3B depicts treatment of HL-60 cells in MTT assay with an extract based on coconut water having very potent cell protection activity as a fermented 2-Stage "ethanol" extract and promoting cell proliferation.
Figure 4:
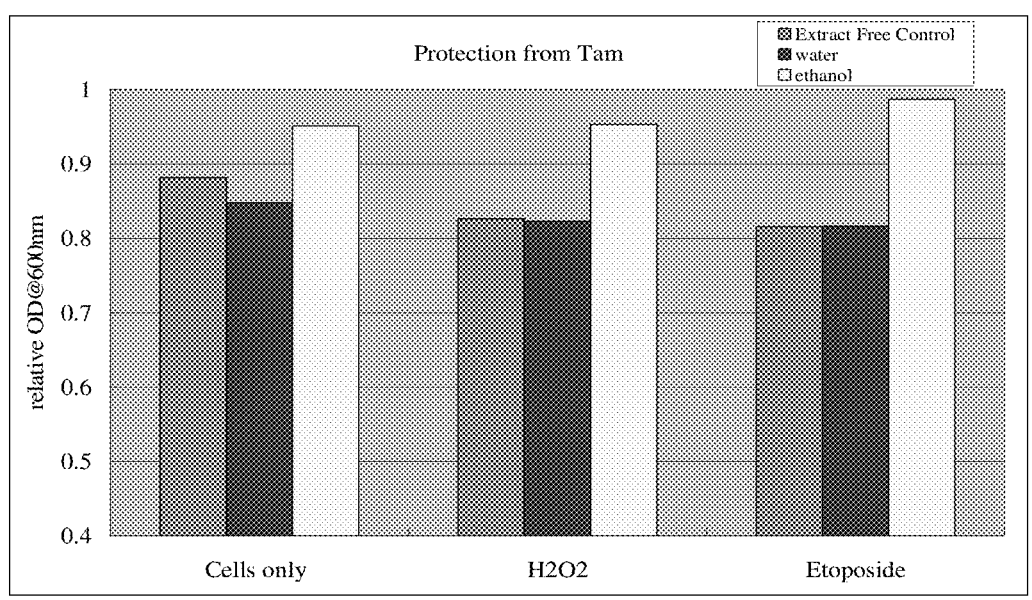
FIG. 4 depicts treatment of HL-60 cells in MTT assay with an extract based on coconut water including tamarillo powder having very potent cell protection activity as a fermented 2-Stage "ethanol" extract and promoting cell proliferation.

In FIGS. 3A, 3B and 4 as shown, the higher the OD the more living cells present. None of the extracts show cytotoxicity as the bar is the same height as the cell only treatment.

The traditional MTT assay was adapted to measure cell protection by an extract. This provides a measure of whether the extract protects cells from stress. HL-60 cells were tested. As exemplified in FIG. 3A, the premise of the assay is as follows:
1. cells only—only has cells growing for 48 hours;
2. cells plus hydrogen peroxide. The cells are grown for 24 hours and then hydrogen peroxide a pro-oxidant is added for a further 24 hours. Hydrogen peroxide is toxic to cells and thus inhibits growth even killing cells;
3. cells plus etoposide. The cells are grown for 24 hours and then etoposide a chemotherapy drug is added for a further 24 hours. Etoposide is very toxic to cells and kills by damaging DNA and preventing cell division and thus cell proliferation. Thus etoposide results in inhibiting cellular growth and ultimately cellular death;
4. extract only is the cells incubated with the extract for 48 hours. If the extract is toxic to the cells then the OD would be lower than the cell only treatment;
5. extract plus hydrogen peroxide the extract is added for 24 hours to the cells and then the hydrogen peroxide is added. If the extract can protect the mitochondria against the oxidative stress (i.e. free radicals) from the hydrogen peroxide then the cells will continue to grow; and
6. extract plus etoposide. The extract is added for 24 hours to the cells and then the etoposide is added. If the extract can protect the DNA against the etoposide chemotherapy then the cells will continue to grow.

Potent extracts such as tamarillo, apple skin, and kawa kawa may be used to assess bioactivity. For example, tamarillo extracts were prepared and either reacted as described above by adding tamarillo powder just before sealing the container (prior to Stage 2), or not reacting but adding tamarillo powder after the reaction was completed (either after Stage 2, or entirely omitting Stage 2). By reacting with the other components it appears that the bioactivity is either enhanced or even changed which is either because the lipids in the reaction mixture are synergistically enhancing bioactivity by acting as a lipid membrane carrier, and/or by esterifying the flavonoids. In the following examples, "water" samples mean that the tamarillo extract or coconut water extract without tamarillo (as in Ex. 2F) was not reacted or fermented in Stage 2, while "ethanol" samples mean that the tamarillo extract or coconut water extract without tamarillo (as in Ex. 2F) was reacted and fermented in Stage 2.

Thus the MTT assay was performed as a standard method using Example 2F without tamarillo (at 1:16 dilution) as a "water" extract, meaning that in this case Stage 2 fermentation was not performed. This extract demonstrated potent efficacy in that it is not cytotoxic and protected the cells from the DNA damaging and free radical stress. It was shown in FIG. 3A that the extract based on coconut water (without tamarillo) has very potent cell protection activity as a "water" extract, and also in FIG. 3B that the extract based on coconut water (without tamarillo) is even more potent as an "ethanol" extract in promoting cell proliferation.

Next, the same assay protocol was performed using the tamarillo extract (Ex. 2F) described above. The tamarillo "water" extract on its own has shown partially reduced cell growth, and has potent cell protection bioactivity against hydrogen peroxide and etoposide. When incorporated into the fermentation reaction to provide a tamarillo "ethanol" extract, there was significant cell proliferation and cell protection, as shown in FIG. 4 (i.e. protection provided from "Tam"). Thus the bioactivity of tamarillo has been synergistically changed by the reaction.

The inventive extracts tested in this example demonstrated potent efficacy in that they are not cytotoxic and have protected the cells from the DNA damaging and free radical stress. It is noted that both hydrogen peroxide and etoposide induce apoptosis. That is how chemotherapy works—it induces DNA damage and then the cell dies. The results from these experiments demonstrate that the inventive extracts have potent cell protection activity, not only against oxidative stress but also against DNA damaging chemotherapy. Therefore these results demonstrated that these extracts protect against induction of apoptosis.

EXAMPLE 8

Immune Assays

Flow cytometry was performed using standard methods to measure cytokine expression using dual labelled antibody markers for IL-10 and TNFα (BioActives Research New Zealand Ltd., Auckland, N.Z.). For this experiment the cells were treated in the following way:

1. cells only—only has cells growing for 48 hours;
2. (control) cells plus lipopolysaccharide (LPS). The cells are grown for 24 hours and then LPS a pro-inflammatory bacterial toxin is added for a further 24 hours;
3. extract only is the cells incubated with the extract for 48 hours; and
4. extract plus LPS. The extract is added for 24 hours to the cells and then the LPS is added.

TABLE 2

| Extract | LPS(−)/ TNF | LPS(−)/ IL-10 | LPS(+)/ TNF | LPS(+)/ IL-10 |
|---|---|---|---|---|
| Control | 19.7 | 13.3 | 31.7 | 9.7 |
| Ex. 2F (Coconut "water"- no tamarillo) | 21.3 | 23.9 | 19.1 | 19.5 |
| Ex. 2F Tamarillo "water" | 22.1 | 24.8 | 19.1 | 20.2 |
| Ex. 2F Tamarillo "ethanol" | 19.9 | 24.8 | 19.3 | 21.5 |

TNF is a proinflammatory cytokine. An increase in TNF indicates inflammation. LPS (lipopolysaccharide) is a bacterial toxin which in this assay was used to induce inflammation (TNF went from an average of 19.9 to 31.7).

IL-10 is an anti-inflammatory cytokine and has been implicated in reducing allergic responses such as eczema. By increasing IL-10, TNF is decreased along with other inflammatory cytokines. LPS also by triggering an increase in TNF results in a cascade that reduces IL-10. As shown in Table 2, coconut and tamarillo extracts prepared in accordance with the invention maintained, in the presence of LPS, TNF expression at a normal level whilst increasing IL-10 to counter the pro-inflammatory attack.

EXAMPLE 9

Acne Cream Formulation

In a further embodiment, an acne treatment cream formulation was prepared.

| Ingredient | Wt (%) |
|---|---|
| Olivem 1000 ECO CERT (Cetearyl Olivate & Sorbitan Olivate) | 7 |
| Aloe vera gel | 2 |
| 2-Stage Extract (modified Example 2C) [2] | 8.5 |
| Hazelnut oil | 2 |
| Blackcurrant oil | 1.5 |
| Kiwifruit seed oil | 1.5 |
| Deionized Water | 70 |
| Bioactive honey (Manuka) | 2 |
| Geogard 221 | 1 |
| Vitamin E | 1 |
| Vitamin C | 0.5 |
| Vitamin A | 0.5 |
| Kiwifruit powder | 1 |
| Totara extract | 0.5 |
| Fragrance | 1 |

[2] no beeswax is included.

Beeswax is omitted since it is not conducive to skin treatment for acne.

Optionally, salicylic acid up to 2.0% of the total weight of the composition may be added. In one embodiment, 0.5% by weight salicylic acid is added.

Totara extract is obtained from tree bark of a native species.

It is expected that the acne cream will successfully treat symptoms associated with acne, and related inflammatory conditions when applied topically. The cream is generally applied topically to the skin in a manner substantially covering the affected surface area. The cream may be formulated as a cosmetic, pharmaceutical, or nutraceutical composition, including a pharmaceutically or nutraceutically acceptable carrier, respectively.

EXAMPLE 10

In a further embodiment, the process for making a pollen-based fermentable composition includes soaking dry pollen grains in coconut water as described above, then incubating for 6 hours at 37.degree. C. Propolis is used as above to stop fermentation, inhibiting enzymes and bacteria alike. The fermented pollen-based composition may be used in formulation, or optionally emulsified into glycerol. The composition may be used, with or without glycerol and other additives, in capsules, face cleansers, shampoos, face toners, and the like.

In an alternative embodiment, freeze drying or spray drying is employed to provide a fermented pollen-based composition.

In an alternative embodiment, the incubation step can be carried out for up to 24 hours, or more.

EXAMPLE 10A

In a further embodiment, the process for making a pollen-based fermentable composition includes soaking dry pollen grains in coconut water as described above, treating the soaked pollen with honey or honeydew at ambient temperature to provide a germinated pollen mixture, then incubating for 6 hours at 37.degree. C. Propolis is used as above to stop fermentation, inhibiting enzymes and bacteria alike. The fermented pollen-based composition may be used in formulation, or optionally emulsified into glycerol. The composition may be used, with or without glycerol and other additives, in capsules, face cleansers, shampoos, face toners, skin creams and the like.

In an alternative embodiment, freeze drying or spray drying is employed to provide a fermented pollen-based composition.

In an alternative embodiment, the incubation step can be carried out for up to 24 hours, or more.

EXAMPLE 10B

In a further embodiment, the process for making a pollen-based fermentable composition includes soaking dry pollen grains in coconut water as described above, treating the soaked pollen with honey or honeydew at ambient temperature to provide a germinated pollen mixture, treating with an enzyme-containing component as described herein, then incubating for 6 to 24 hours at 37.degree. C. Propolis is used as above to stop fermentation, inhibiting enzymes and bacteria alike. The fermented pollen-based composition is available as MYRIPHYTASE.™. (available from Bionona Ltd., Auckland, New Zealand). The fermented pollen-based composition may be used in formulation, or optionally emulsified into glycerol. The composition may be used, with or without glycerol and other additives, in capsules, shampoos, conditioners, skin creams and the like.

In an alternative embodiment, a probiotic component is added prior to incubation. Useful probiotic components include *Bacillus* spp., *Lactobacillus* spp., variants and strains thereof, or mixtures thereof. Freeze dried bacteria including, but not limited to, *Bacillus* spp., *Lactobacillus* spp., variants and strains thereof, or mixtures thereof, are contemplated. These compositions may be used, with or without glycerol and other additives, in capsules, shampoos, conditioners, skin creams and the like.

In an alternative embodiment, freeze drying or spray drying is employed to provide a fermented pollen-based composition.

In an alternative embodiment, coconut oil is added to the reaction mixture.

In an alternative embodiment, the incubation step can be carried out for up to 24 hours, or more.

EXAMPLE 10C

Anaerobic Fermentation

In a further embodiment, the process for making a pollen-based fermentable composition includes soaking dry pollen grains in coconut water as described above; optionally treating the soaked pollen with honey or honeydew at ambient temperature to provide a germinated pollen mixture; and optionally treating with an enzyme-containing component as described herein. Next, an oil or melted beeswax is poured in a sealing layer on top of the germinated pollen mixture which creates and thus provides an anaerobic medium and an environment conducive for fermentation. Incubation which effects fermentation is carried out for 12 to 24 hours at 37.degree. C. Propolis is used as above to stop fermentation, inhibiting enzymes and bacteria alike.

As described herein, purified beeswax is melted at 65.degree. C. and poured on top of the reaction mixture to provide the sealing layer.

Useful oils for providing the sealing layer include, but are not limited to, coconut oil, olive oil, kiwi fruit oil, kiwi fruit seed oil, hemp oil, avocado oil, or mixtures thereof, and the like.

After incubation, the top sealing layer of beeswax or oil is removed, with the exception of coconut oil which is miscible. The fermented pollen-based composition may be used in formulation, or optionally emulsified into glycerol. The fermented composition may be used, with or without glycerol and other additives, in capsules, shampoos, conditioners, skin creams and the like.

The cosmetic (or cosmeceutical), or nutraceutical compositions of the present invention may be administered in combination with a nutraceutically acceptable carrier. The active ingredients in such formulations may comprise from 1% by weight to 99% by weight, or alternatively, 0.1% by weight to 99.9% by weight. Alternatively, the active ingredients can range from about 5% by weight to about 75% by weight, or from about 10% by weight to about 75% by weight. "Nutraceutically acceptable carrier" means any carrier, diluent or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

The topical pharmaceutical compositions of the present invention may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user.

In accordance with certain embodiments, the topical pharmaceutical compositions disclosed herein can be provided in the form of an ointment, cream, lotion, gel or other transdermal delivery systems as described in L. V. Allen, Jr., et al., *Ansel's Pharmaceutical Dosage Forms and Drug Delivery Systems*, 9$^{th}$ Ed., pp. 272-293 (Philadelphia, Pa.: Lippincott Williams & Wilkins, 2011) which is incorporated herein by reference.

Ointments, as used herein, refer to semi-solid preparations including an ointment base having one or more active ingredients incorporated or fused (i.e., melted together with other components of the formulation and cooled with constant stirring to form a congealed preparation) therein. The ointment base may be in the form of: an oleaginous or hydrocarbon base (e.g., petrolatum or a petrolatum/wax combination); an absorption base which permits the incorporation of aqueous solution resulting in the formation of a water-in-oil emulsion (e.g., hydrophilic petrolatum) or which is a water-in-oil emulsion that permits the incorporation of additional quantities of aqueous solutions (e.g., lanolin); a water-removable base which are oil-in-water emulsions that may be diluted with water or aqueous solutions (e.g., hydrophilic ointment, USP); or a water-soluble base that do not contain oleaginous components (e.g., polyethylene glycol (PEG) formulations which combine PEGs having an average molecular below 600 with a PEG having an average molecular weight above 1,000); and the like.

Creams, as used herein, refer to semisolid preparations containing one or more active, fermented pollen-based material, or medicinal agent dissolved or dispersed in either a water-in-oil emulsion or an oil-in-water emulsion or in another type of water-washable base. Generally, creams are differentiated from ointments by the ease with which they are applied/spread onto a surface such as the skin and the ease with which they are removed from a treated surface.

Lotions, as used herein, refer to suspensions of solid materials in an aqueous vehicle. Generally, lotions have a non-greasy character and increased spreadability over large areas of the skin than ointments, creams, and gels.

Gels, as used herein, refer to semisolid systems including a dispersion of small and/or large molecules in an aqueous liquid vehicle which is rendered jellylike by the addition of a gelling agent. Suitable gelling agents include, but are not limited to, synthetic macromolecules (e.g., carbomer polymers), cellulose derivatives (e.g., carboxymethylcellulose and/or hydroxypropyl methylcellulose), and natural gums (e.g., tragacanth gum, carrageenan, and the like). Gel preparations may be in the form of a single-phase gel in which the active or medicinal ingredients are uniformly dispersed throughout the liquid vehicle without visible boundaries or a two-phase gel wherein flocculants or small distinct particles of the active or medicinal ingredient are dispersed within the liquid vehicle.

Transdermal preparations may be formed from an ointment, cream, or gel that has been combined with a penetration enhancer and are designed to deliver an active or medicinal ingredient systemically. Penetration enhancers include, for example, dimethyl sulfoxide, ethanol, propylene glycol, glycerine, PEG, urea, dimethyl acetamide, sodium lauryl sulfate, poloxamers, Spans, Tweens, lecithin, and/or terpenes amongst others.

Other suitable semi-solid forms for use as cosmetic and/or topical pharmaceutical compositions include pastes (preparations containing a larger proportion of solid material rendering them stiffer than ointments) and glycerogelatins (plastic masses containing gelatin, glycerine, water, and an active or medicinal ingredient).

In other embodiments the topical and/or cosmetic compositions can be prepared in accordance with dosage forms as described in *Sample Preparation of Pharmaceutical Dosage Forms,* B. Nickerson, Ed. (New York: Springer, 2011) herein incorporated by reference.

In addition, shampoos or other types of cleansing products are contemplated. Also, topical sprays are contemplated including sprays useful for one or more applications to the skin, back, neck, arms, legs, and torso, for example.

For oral administration, fermented pollen-based extract, or a solid formulation thereof such as lyophilized powder, may be combined with one or more solid inactive ingredients for the preparation of tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

Routes of Administration

The fermented pollen-based extract may be administered by any route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, topical spray, or subcutaneous administration.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about five weeks. The treatment schedule may be repeated as required.

Furthermore, it is believed that this technology and process may be applied to other reaction platforms. The aforementioned examples describe a technology platform in which different starting materials can be added depending on the desired end product. By altering the settings, e.g. aerobic/anaerobic, temperature and pressure different end product compounds are obtained. The end products resulting from the reaction platform are analogous to those produced in nature. These compounds mimic those in nature which control immune and cell death signaling pathways and can be used to treat a range of immune and apoptosis related diseases.

In an alternative embodiment, a technology platform may comprise a bioreactor, that uses naturally occurring chemical reactions to produce modified or new bioactive compounds that regulate mammalian cell signaling. These chemical reactions can be applied to any plant, microbial, marine or insect derived extract to create bioactive components that interact directly with the human signaling pathways to regulate immune and cell death responses.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A fermented pollen-based composition made by a process comprising
    treating pollen grains with one or more natural potassium sources selected from the group consisting of coconut water, coconut milk, raw honey, and honeydew honey, to naturally stimulate germination of the pollen to form a germinated pollen, then
    incubating the germinated pollen to form a fermented pollen-based composition,
    wherein the resulting composition after the step of incubating comprises a plurality of bioactive components selected from low molecular weight peptides, fatty acids, esterified flavonoids, dicaffeoyl quinic acid isomers and dicaffeoyl tartaric acid ester or ether compounds.

2. The fermented pollen-based composition of claim 1, wherein the germinated pollen is incubated with one or more additional components selected from beeswax, oils, enzyme-containing components derived from fruit, and probiotic components.

3. The fermented pollen-based composition of claim 1, wherein the composition is freeze dried or spray dried.

4. The fermented pollen-based composition of claim 1, wherein the dicaffeoyl quinic acid isomers are selected from the group consisting of 1,3-diCQA, 1,4-diCQA, 1,5-diCQA, 3,4-diCQA, 3,5-diCQA, and 4,5-diCQA.

5. The fermented pollen-based composition of claim 1, wherein the fatty acids are selected from the group consisting of lauric acid, myristic acid, palmitic acid, palmitoleic acid, stearic acid, oleic acid, linoleic acid, GLA, linolenic acid, behenic acid, and ligoceric acid.

6. A topical skin composition comprising an effective amount of the fermented pollen-based composition of claim 1 as an active ingredient.

7. The topical skin composition of claim 6, comprising about 1-10% by weight of the fermented pollen-based composition and one or more pharmaceutically or nutraceutically acceptable carriers, diluents and/or excipients.

8. The topical skin composition of claim 7, wherein the fermented pollen-based composition is emulsified into glycerol.

9. The topical skin composition of claim 7, wherein the composition is a cream, lotion, gel, ointment, paste, cleanser, toner, shampoo, or conditioner.

10. The topical skin composition of claim 7, wherein the composition comprises an emulsifying oil containing cetearyl olivate and sorbitan olivate.

11. The topical skin composition of claim 7, wherein the composition comprises at least one botanical oil component selected from shea butter, safflower oil, macadamia nut oil, hazel nut oil, blackcurrant oil, kiwifruit seed oil, grape seed oil, argan oil, jojoba oil, and mixtures thereof.

12. The topical skin composition of claim 11, wherein the botanical oil component is present in an amount of about 5-7% by weight based on the total weight of the composition.

13. The topical skin composition of claim 7, wherein the composition comprises water as a carrier in an amount of about 70% by weight based on the total weight of the composition.

14. The topical skin composition of claim 6, wherein the composition is for treating a skin condition selected from the group consisting of eczema, psoriasis, dermatitis, rosacea, acne, actinic keratosis (AK), moles, age spots, wrinkles, wounds, lacerations, scars, photodamage, herpes, corpus molluscum, and lupus.

* * * * *